United States Patent
Petersen

(10) Patent No.: US 10,953,145 B2
(45) Date of Patent: Mar. 23, 2021

(54) DRIVELINE CONNECTORS AND METHODS FOR USE WITH HEART PUMP CONTROLLERS

(71) Applicant: TC1 LLC, St. Paul, MN (US)

(72) Inventor: Ethan Petersen, Oakland, CA (US)

(73) Assignee: TCI LLC, St. Paul, MN (US)

( * ) Notice: Subject to any disclaimer, the term of this patent is extended or adjusted under 35 U.S.C. 154(b) by 125 days.

(21) Appl. No.: 16/270,907

(22) Filed: Feb. 8, 2019

(65) Prior Publication Data
US 2019/0290816 A1    Sep. 26, 2019

Related U.S. Application Data

(60) Provisional application No. 62/646,152, filed on Mar. 21, 2018.

(51) Int. Cl.
*A61M 1/12*    (2006.01)
*A61M 1/10*    (2006.01)
(Continued)

(52) U.S. Cl.
CPC ........ *A61M 1/1008* (2014.02); *A61M 1/1086* (2013.01); *A61M 1/122* (2014.02);
(Continued)

(58) Field of Classification Search
CPC .. A61M 1/1008; A61M 1/101; A61M 1/1086; A61M 1/122; A61M 1/127;
(Continued)

(56) References Cited

U.S. PATENT DOCUMENTS 3,882,861 A    5/1975 Kettering
4,521,871 A    6/1985 Galdun et al.
(Continued)

FOREIGN PATENT DOCUMENTS

WO    2006055745 A2    5/2006
WO    2010122139 A1    10/2010
(Continued)

OTHER PUBLICATIONS

HeartMate II , "The HeartMate II system", HeartMate II, Left Ventricular Assist System, Retrieved from Internet : http://heartmateii.com/heartmate-ii-system.aspx, Jul. 16, 2015, 2 pages.
(Continued)

*Primary Examiner* — George Manuel
(74) *Attorney, Agent, or Firm* — Kilpatrick Townsend & Stockton LLP

(57) ABSTRACT

A connector assembly for connecting external power sources to an implanted medical device enables continual supply of electrical power to the implanted medical device during replacement of an external power source. A connector assembly includes a distal driveline contact assembly, a first driveline contact assembly, and a second driveline contact assembly. The second driveline contact assembly is connectable to the distal driveline contact assembly prior to disconnection of the first driveline contact assembly from the distal driveline contact assembly.

21 Claims, 12 Drawing Sheets

(51) Int. Cl.
*H01R 35/04* (2006.01)
*H01R 13/6581* (2011.01)
*H01R 43/26* (2006.01)
*H01R 13/15* (2006.01)

(52) U.S. Cl.
CPC ............ *A61M 1/127* (2013.01); *H01R 13/15* (2013.01); *H01R 13/6581* (2013.01); *H01R 35/04* (2013.01); *H01R 43/26* (2013.01); *A61M 1/101* (2013.01); *A61M 2205/8206* (2013.01); *H01R 2201/12* (2013.01)

(58) Field of Classification Search
CPC ........... A61M 2205/8206; H01R 13/15; H01R 13/6581; H01R 2201/12; H01R 35/04; H01R 43/26
See application file for complete search history.

(56) References Cited

U.S. PATENT DOCUMENTS

| | | | |
|---|---|---|---|
| 5,046,965 | A | 9/1991 | Neese et al. |
| 5,695,474 | A | 12/1997 | Daugherty |
| 5,888,242 | A | 3/1999 | Antaki et al. |
| 5,935,105 | A | 8/1999 | Manning et al. |
| 5,991,595 | A | 11/1999 | Romano et al. |
| 6,071,093 | A | 6/2000 | Hart |
| 6,116,862 | A | 9/2000 | Rau et al. |
| 6,146,179 | A | 11/2000 | Denny et al. |
| 6,183,412 | B1 | 2/2001 | Benkowski et al. |
| 6,234,772 | B1 | 5/2001 | Wampler et al. |
| 6,264,635 | B1 | 7/2001 | Wampler et al. |
| 6,305,962 | B1 | 10/2001 | Maher et al. |
| 6,494,736 | B2 | 12/2002 | Mito et al. |
| 6,592,620 | B1 | 7/2003 | Lancisi et al. |
| 6,688,861 | B2 | 2/2004 | Wampler |
| 7,340,304 | B2 | 3/2008 | MacDonald et al. |
| 7,425,142 | B1 | 9/2008 | Putz et al. |
| 7,658,613 | B1 | 2/2010 | Griffin et al. |
| 7,699,586 | B2 | 4/2010 | LaRose et al. |
| 7,961,156 | B2 | 6/2011 | Knott et al. |
| 7,976,271 | B2 | 7/2011 | LaRose et al. |
| 7,997,854 | B2 | 8/2011 | LaRose et al. |
| 8,007,254 | B2 | 8/2011 | LaRose et al. |
| 8,029,441 | B2 | 10/2011 | Mazza et al. |
| 8,152,493 | B2 | 4/2012 | LaRose et al. |
| 8,157,720 | B2 | 4/2012 | Marseille et al. |
| 8,186,665 | B2 | 5/2012 | Akema |
| 8,323,174 | B2 | 12/2012 | Jeevanandam et al. |
| 8,344,847 | B2 | 1/2013 | Moberg et al. |
| 8,348,678 | B2 | 1/2013 | Hardisty et al. |
| 8,449,444 | B2 | 5/2013 | Poirier |
| 8,506,471 | B2 | 8/2013 | Bourque |
| 8,562,508 | B2 | 10/2013 | Dague et al. |
| 8,597,350 | B2 | 12/2013 | Rudser et al. |
| 8,628,460 | B2 | 1/2014 | Yomtov et al. |
| 8,639,348 | B2 | 1/2014 | Geheb |
| 8,652,024 | B1 | 2/2014 | Yanai et al. |
| 8,657,733 | B2 | 2/2014 | Ayre et al. |
| 8,668,473 | B2 | 3/2014 | LaRose et al. |
| 8,684,763 | B2 | 4/2014 | White et al. |
| 8,894,561 | B2 | 11/2014 | Callaway et al. |
| 8,971,958 | B2 | 3/2015 | Frikart et al. |
| 9,302,035 | B2 | 4/2016 | Flaherty et al. |
| 9,985,374 | B2 | 5/2018 | Hodges |
| 10,124,101 | B2 | 11/2018 | Wong et al. |
| 2002/0007198 | A1 | 1/2002 | Haupert et al. |
| 2005/0071001 | A1 | 3/2005 | Jarvik |
| 2007/0078293 | A1 | 4/2007 | Shambaugh et al. |
| 2007/0142696 | A1 | 6/2007 | Crosby et al. |
| 2008/0021394 | A1 | 1/2008 | Larose et al. |
| 2009/0118827 | A1 | 5/2009 | Sugiura |
| 2009/0203957 | A1 | 8/2009 | Larose et al. |
| 2011/0160516 | A1 | 6/2011 | Dague et al. |
| 2011/0218383 | A1 | 9/2011 | Broen et al. |
| 2012/0028490 | A1 | 2/2012 | Litzler et al. |
| 2012/0046514 | A1 | 2/2012 | Bourque |
| 2012/0059443 | A1* | 3/2012 | Sabin ................ H01R 4/5008 607/116 |
| 2012/0095281 | A1 | 4/2012 | Reichenbach et al. |
| 2012/0172657 | A1 | 7/2012 | Marseille et al. |
| 2012/0183261 | A1 | 7/2012 | Schwandt et al. |
| 2013/0096364 | A1 | 4/2013 | Reichenbach et al. |
| 2013/0121821 | A1 | 5/2013 | Ozaki et al. |
| 2013/0127253 | A1 | 5/2013 | Stark et al. |
| 2013/0170970 | A1 | 7/2013 | Ozaki et al. |
| 2013/0225909 | A1 | 8/2013 | Dormanen et al. |
| 2013/0314047 | A1 | 11/2013 | Eagle et al. |
| 2014/0073838 | A1 | 3/2014 | Dague et al. |
| 2014/0194985 | A1 | 7/2014 | Vadala, Jr. |
| 2014/0243970 | A1 | 8/2014 | Yanai |
| 2014/0309733 | A1 | 10/2014 | Cotter et al. |
| 2015/0038771 | A1 | 2/2015 | Marseille et al. |
| 2016/0095968 | A1 | 4/2016 | Rudser |
| 2018/0055983 | A1 | 3/2018 | Bourque |
| 2018/0250459 | A1 | 9/2018 | Kimball et al. |
| 2018/0256796 | A1 | 9/2018 | Hansen |
| 2018/0256800 | A1 | 9/2018 | Conyers et al. |
| 2018/0256801 | A1 | 9/2018 | Conyers et al. |

FOREIGN PATENT DOCUMENTS

| | | |
|---|---|---|
| WO | 2011081626 A1 | 7/2011 |
| WO | 2014107424 A2 | 7/2014 |
| WO | 2015017770 A1 | 2/2015 |
| WO | 2017087380 A1 | 5/2017 |

OTHER PUBLICATIONS

My LVAD, "Berlin Heart Incor", Retrieved from Internet:http://www.mylvad.com/content/berlin-heart-incor, Jul. 16, 2015, 3 pages.
Di Paola et al., "Improved Blood Pump Connectors", U.S. Appl. No. 16/395,134, filed Apr. 25, 2019, Unpublished, 94 pages.

* cited by examiner

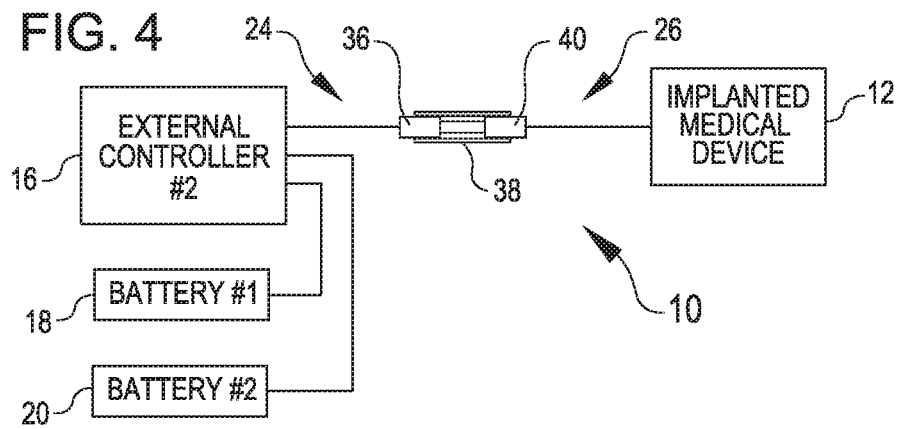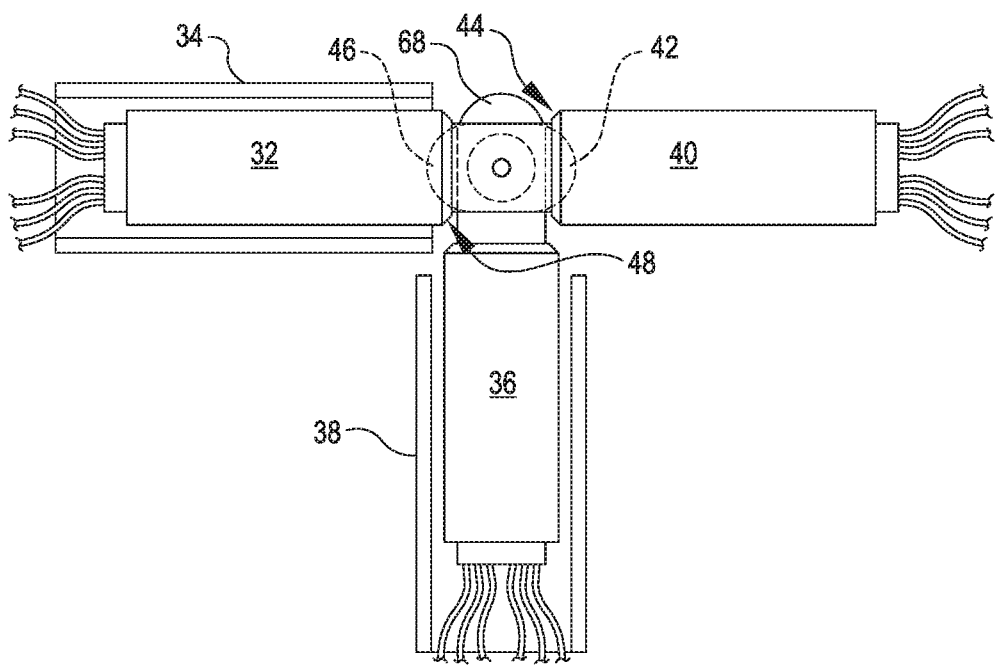

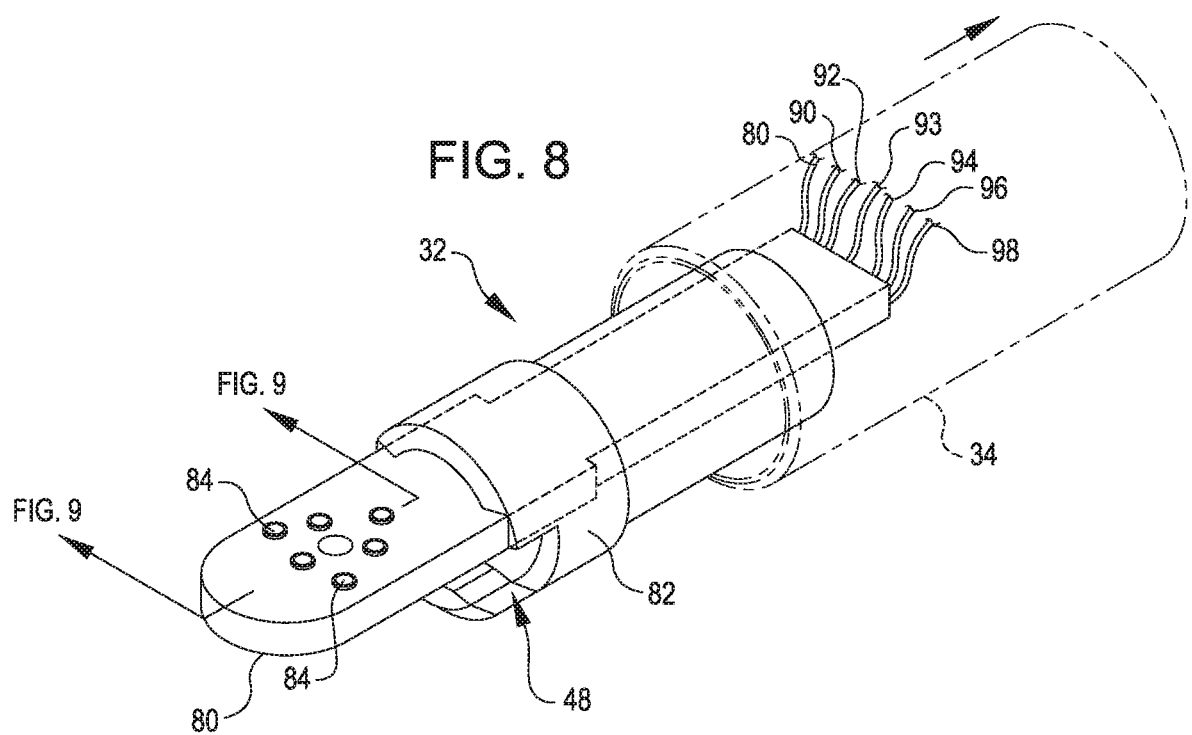
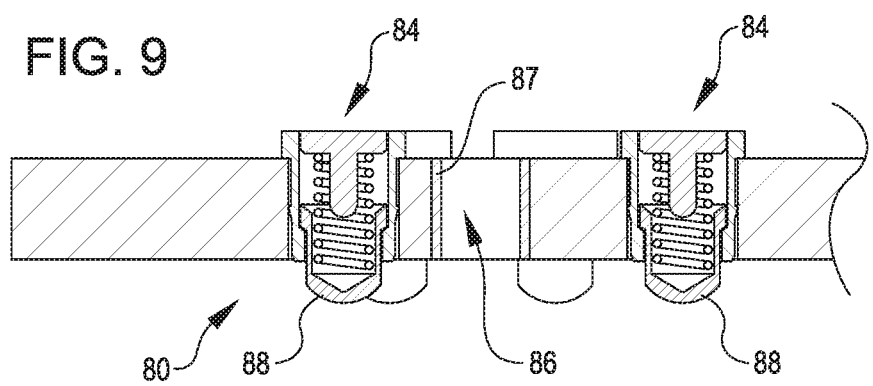

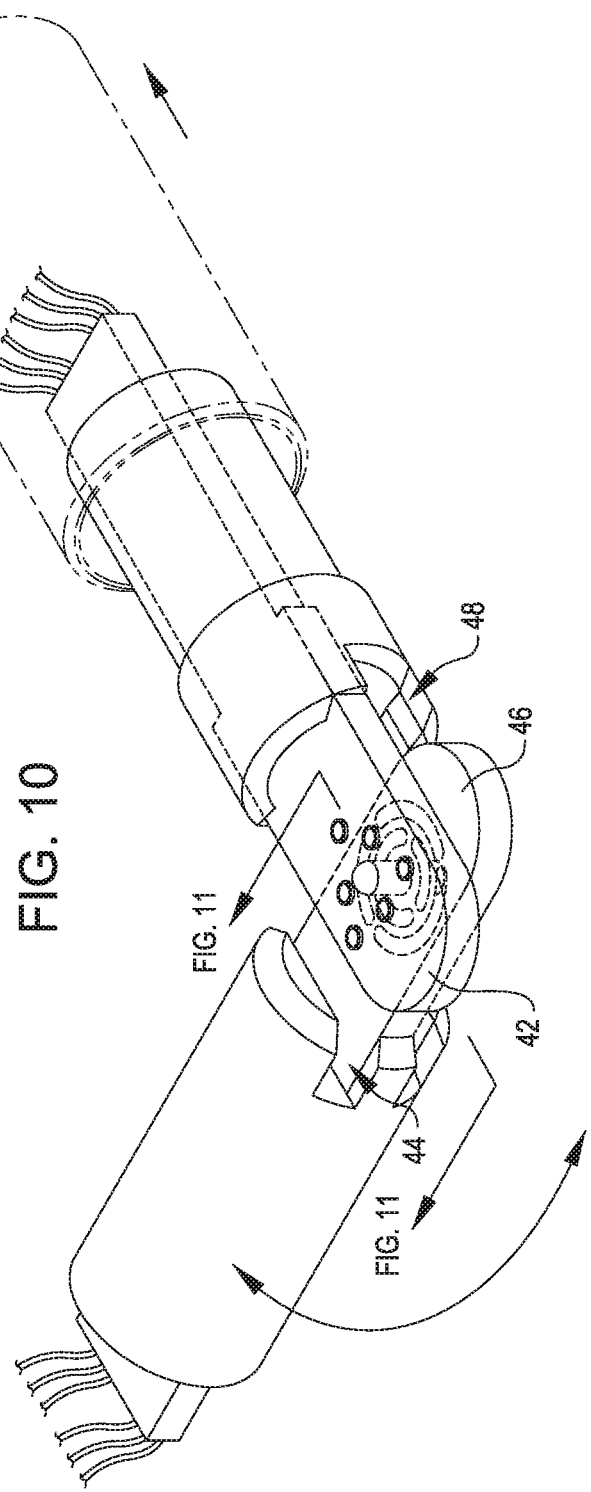

DRIVELINE CONNECTORS AND METHODS FOR USE WITH HEART PUMP CONTROLLERS

CROSS REFERENCE TO RELATED APPLICATIONS

The present application claims the benefit under 35 USC § 119(e) of U.S. Provisional Appln. No. 62/646,152 filed Mar. 21, 2018; the full disclosure which is incorporated herein by reference in its entirety for all purposes.

BACKGROUND

Ventricular assist devices, known as VADs, often include an implantable blood pump and are used for both short-term (i.e., days, months) and long-term applications (i.e., years or a lifetime) where a patient's heart is incapable of providing adequate circulation, commonly referred to as heart failure or congestive heart failure. According to the American Heart Association, more than five million Americans are living with heart failure, with about 670,000 new cases diagnosed every year. People with heart failure often have shortness of breath and fatigue. Years of living with blocked arteries and/or high blood pressure can leave a heart too weak to pump enough blood to the body. As symptoms worsen, advanced heart failure develops.

A patient suffering from heart failure may use a VAD while awaiting a heart transplant or as a long term therapy. A patient may also use a VAD while recovering from heart surgery. Thus, a VAD can supplement a weak heart (i.e., partial support) or can effectively replace the natural heart's function.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

In many embodiments, a connector assembly for connecting a first external controller and/or power supply to an implanted medical device is configured for connection of a second external controller and/or power supply to the implanted medical device while the first external controller and/or power supply is connected to the implanted medical device. After the second external controller and/or power supply is connected to the implanted medical device, the first external controller and/or power supply can be disconnected from the implanted medical device. As a result, the connector assembly enables continued control of the implanted medical device and/or supply of electrical power to the implanted medical device during replacement of the first external controller and/or power supply with the second external controller and/or power supply. The connector assembly can be used with any suitable implanted medical device, and can be especially beneficial when used with an implanted blood pump to maintain control and/or operation of the implanted blood pump during replacement of an external controller and/or power supply operatively coupled with the implanted blood pump.

Thus, in one aspect, a method is provided for replacing a first external power supply that supplies electrical power to an implanted medical device with a second external power supply that supplies electrical power to the implanted medical device without interrupting supply of electrical power to the implanted medical device from at least one of the first external power supply and the second external power supply. The method includes supplying electrical power to the implanted medical device from the first external power supply via a first driveline connected to the first external power supply and a distal driveline connected to the implanted medical device. The first driveline includes a first driveline contact assembly. The distal driveline includes a distal driveline contact assembly that, when connected to the first driveline contact assembly, can receive electrical power from the first external power supply via the first driveline contact assembly. The method includes operatively connecting the second external power supply to the implanted medical device while the first external power supply is operatively connected to the implanted medical device. For example, while the first driveline contact assembly is connected to the distal driveline contact assembly, a second driveline contact assembly can be connected to the distal driveline contact assembly. In many embodiments, the second driveline contact assembly is included in a second driveline connected to the second external power supply. The method includes disconnecting the first external power supply from the implanted medical device while the second external power supply is operatively coupled to the implanted medical device. For example, in many embodiments, the first driveline contact assembly is disconnected from the distal driveline contact assembly while the second driveline contact assembly remains connected to the distal driveline contact assembly.

In many embodiments, the method for replacing the first external power supply with the second external power supply includes reconfiguring a shield assembly from a retention configuration to a connection configuration. In the retention configuration, the shield assembly prevents disconnection of the first driveline contact assembly from the distal driveline contact assembly. In the connection configuration, the shield assembly accommodates the first driveline contact assembly and the second driveline contact assembly being connected to the distal driveline contact assembly at the same time. In the connection configuration, the shield assembly accommodates disconnection of the first driveline contact assembly from the distal driveline contact assembly. In many embodiments, the method includes, subsequent to the disconnection of the first driveline contact assembly from the distal driveline contact assembly, reconfiguring the shield assembly from the connection configuration to the retention configuration. In the retention configuration, the shield assembly prevents disconnection of the second driveline contact assembly from the distal driveline contact assembly.

In many embodiments, the method for replacing the first external power supply with the second external power supply includes rotating the first driveline contact assembly relative to the distal driveline contact assembly and rotating the second driveline contact assembly relative to the distal driveline contact assembly. For example, in many embodiments, the method includes, prior to the disconnection of the first driveline contact assembly from the distal driveline contact assembly, rotating the first driveline contact assembly relative to the distal driveline contact assembly from a retention orientation for the first driveline contact assembly to a connection orientation for the first driveline contact assembly. In the retention orientation for the first driveline contact assembly, engagement of the first driveline contact assembly with the distal driveline contact assembly blocks disconnection of the first driveline external connector from the distal driveline contact assembly. In the connection orientation for the first driveline contact assembly, lack of blocking engagement between the first driveline contact assembly with the distal driveline contact assembly accommodates disconnection of the first driveline contact assembly from the distal driveline contact assembly. In many embodiments, the method includes, prior to the reconfiguration of the shield assembly from the connection configuration to the retention configuration, rotating the second driveline contact assembly relative to the distal driveline contact assembly from a connection orientation for the second driveline contact assembly to a retention orientation for the second driveline contact assembly. In the connection orientation for the second driveline contact assembly, lack of blocking engagement of the second driveline contact assembly with the distal driveline contact assembly accommodates connection of the second driveline contact assembly with the distal driveline contact assembly. In the retention orientation for the second driveline contact assembly, engagement between the second driveling contact assembly with the distal driveline contact assembly blocks disconnection of the second driveline contact assembly from the distal driveline contact assembly.

In many embodiments of the method for replacing the first external power supply with the second external power supply, the shield assembly is translated relative to one of the first driveline contact assembly and the distal driveline contact assembly. For example, in many embodiments of the method, the reconfiguration of the shield assembly from the retention configuration to the connection configuration includes translating the shield assembly relative to one of the first driveline contact assembly and the distal driveline contact assembly to disengage the shield assembly from the other of the first driveline contact assembly and the distal driveline contact assembly. In many embodiments of the method, the reconfiguration of the shield assembly from the connection configuration to the retention configuration includes translating the shield assembly relative to one of the second driveline contact assembly and the distal driveline contact assembly to engage the shield assembly with the other of the second driveline contact assembly and the distal driveline contact assembly.

In many embodiments of the method for replacing the first external power supply with the second external power supply, the each of the first driveline contact assembly and the second driveline contact assembly is rotationally coupled with the distal driveline contact assembly. For example, in many embodiments of the method, the disconnection of the first driveline contact assembly from the distal driveline contact assembly includes removing a first protruding pin of the distal driveline contact assembly from a recess of the first driveline contact assembly. Electrical contacts of the first driveline contact assembly are aligned with first electrical contacts of the distal driveline contact assembly when the first protruding pin is disposed in the recess of the first driveline contact assembly. In many embodiments of the method, the connection of the second driveline contact assembly to the distal driveline contact assembly includes inserting a second protruding pin of the distal driveline contact assembly into a recess of the second driveline contact assembly to align electrical contacts of the second driveline contact assembly with second electrical contacts of the distal driveline contact assembly. In many embodiments, the method further includes maintaining contact between the electrical contacts of the second driveline contact assembly and the second electrical contacts of the distal driveline contact assembly during the rotation of the second driveline contact assembly relative to the distal driveline contact assembly.

The method for replacing the first external controller with the second external controller can be used in connection with any suitable implanted medical device. For example, in many embodiments of the method, the implanted medical device includes a blood pump.

In another aspect, a blood circulation assist system includes an implantable blood pump, a first external controller, a first driveline, a first driveline contact assembly, a second external controller, a second driveline, a second driveline contact assembly, a distal driveline, and a distal driveline contact assembly. The first driveline is connected to the first external controller. Electrical power is transmittable via the first external controller to the implantable blood pump through the first driveline. The first driveline contact assembly is electrically connected to the first driveline. The second driveline is connected to the second external controller. Electrical power is transmittable via the second external controller to the implantable blood pump through the second driveline. The second driveline contact assembly is electrically connected to the second driveline. The distal driveline is connected to the implantable blood pump. Electrical power is transmittable to the implantable blood pump through the distal driveline. The distal driveline contact assembly is electrically connected to the distal driveline. The distal driveline contact assembly is electrically connectable to: (a) either of the first driveline contact assembly and the second driveline contact assembly; and (b) either of the first driveline contact assembly and the second driveline contact assembly while being connected to the other of the first driveline contact assembly and the second driveline contact assembly.

In many embodiments of the blood circulation assist system, each of the first driveline contact assembly and the second driveline contact assembly is rotatable relative to the distal driveline contact assembly between a retention orientation for the respective driveline first or second driveline contact assembly and a connection orientation for the respective first or second driveline contact assembly. For example, in many embodiments, while the first driveline contact assembly is connected to the distal driveline contact assembly, the first driveline contact assembly is rotatable relative to the distal driveline contact assembly between a retention orientation for the first driveline contact assembly and a connection orientation for the first driveline contact assembly. In many embodiments, while the first driveline contact assembly is connected to the distal driveline contact assembly and in the retention orientation for the first driveline contact assembly, engagement of the first driveline contact assembly with the distal driveline contact assembly blocks disconnection of the first driveline contact assembly from the distal driveline contact assembly. In many embodiments, while the first driveline contact assembly is in the connection orientation for the first driveline contact assembly, lack of engagement of the first driveline contact assembly with the distal driveline contact assembly accommodates disconnection of the first driveline contact assembly from the distal driveline contact assembly and connection of the first driveline contact assembly with the distal driveline contact assembly. In many embodiments, while the second driveline contact assembly is connected to the distal driveline contact assembly, the second driveline contact assembly is rotatable relative to the distal driveline contact assembly between a connection orientation for the second driveline contact assembly and a retention orientation for the second driveline contact assembly. In many embodiments, while the second driveline contact assembly is in the connection orientation for the second driveline contact assembly, lack of engagement of the second driveline contact assembly with the distal driveline contact assembly accommodates connection of the second driveline contact assembly with the distal driveline contact assembly and disconnection of the second driveline contact assembly from the distal driveline contact assembly. In many embodiments, while the second driveline contact assembly is connected to the distal driveline contact assembly and in the retention orientation for the second driveline contact assembly, engagement of the second driveline contact assembly with the distal driveline contact assembly blocks disconnection of the second driveline contact assembly from the distal driveline contact assembly.

In many embodiments, the blood circulation assist system includes a shield assembly that is reconfigurable between a retention configuration and a connection configuration. In many embodiments, while the shield assembly is in the retention configuration and the first driveline contact assembly is connected to the distal driveline contact assembly: (a) the shield assembly interfaces with each of the first driveline contact assembly and distal driveline contact assembly, and keeps the first driveline contact assembly in the retention orientation for the first driveline contact assembly; and (b) the shield assembly blocks connection of the second driveline contact assembly to the distal driveline contact assembly. In many embodiments, while the shield assembly is in the connection configuration and the first driveline contact assembly is connected to the distal driveline contact assembly: (a) the shield assembly accommodates connection of the second driveline contact assembly to the distal driveline contact assembly; and (b) the shield assembly accommodates disconnection of the first driveline contact assembly from the distal driveline contact assembly. In many embodiments, while the shield assembly is in the retention configuration and the second driveline contact assembly is connected to the distal driveline contact assembly: (a) the shield assembly interfaces with each of the second driveline contact assembly and distal driveline contact assembly, and keeps the second driveline contact assembly in the retention orientation for the second driveline contact assembly; and (b) the shield assembly blocks connection of the first driveline contact assembly to the distal driveline contact assembly.

In many embodiments of the blood circulation assist system, each of the first driveline contact assembly and the second driveline contact assembly is rotationally coupled with the distal driveline contact assembly when connected to the distal driveline contact assembly. For example, in many embodiments of the blood circulation assist system, the distal driveline contact assembly includes a first pin, first side electrical contacts, a second pin, and second side electrical contacts. The first pin protrudes perpendicular to a first side of the distal driveline contact assembly. The first side electrical contacts are disposed on the first side of the distal driveline contact assembly. The second pin protrudes perpendicular to a second side of the distal driveline contact assembly. The second side electrical contacts are disposed on the second side of the distal driveline contact assembly. In many embodiments of the blood circulation assist system, the first driveline contact assembly includes first driveline electrical contacts and a receptacle for the first pin. The receptacle for the first pin is sized to receive and interface with the first pin so as to rotationally coupled the first driveline contact assembly with the distal driveline contact assembly. The receptacle for the first pin is positioned to align the first driveline electrical contacts with the first side electrical contacts. In some embodiments of the blood circulation assist system, engagement of the first driveline contact assembly with the distal driveline first retention feature while the first driveline contact assembly is connected to the distal driveline contact assembly and in the retention orientation for the first driveline contact assembly blocks disengagement of the first driveline electrical contacts from the first side electrical contacts. In many embodiments of the blood circulation assist system, the second driveline contact assembly includes second driveline electrical contacts and a receptacle for the second pin. The receptacle for the second pin is sized to receive and interface with the second pin so as to rotationally couple the second driveline contact assembly with the distal driveline contact assembly. The receptacle for the second pin is positioned to align the second driveline electrical contacts with the second side electrical contacts. In some embodiments of the blood circulation assist system, engagement of the second driveline contact assembly with the distal driveline contact assembly while the second driveline contact assembly is connected to the distal driveline contact assembly and in the retention orientation for the second driveline contact assembly blocks disengagement of the second driveline electrical contacts from the second side electrical contacts.

In many embodiments of the blood circulation assist system, electrical connection between the distal driveline and each of the first driveline and the second driveline can be maintained during rotation of each of the first driveline connector assembly and the second driveline connector assembly relative to the distal driveline connector assembly. For example, in some embodiments of the blood circulation assist system, each of the first side electrical contacts extends along a respective circular arc so that contact can be maintained between the first side electrical contact and a respective one of the first driveline electrical contacts while the first driveline contact assembly is rotated relative to the distal driveline contact assembly between the retention orientation for the first driveline contact assembly and the connection orientation for the first driveline contact assembly. In some embodiments of the blood circulation assist system, each of the second side electrical contacts extends along a respective circular arc so that contact can be maintained between the second side electrical contact and a respective one of the second driveline electrical contacts while the second driveline contact assembly is rotated relative to the distal driveline contact assembly between the connection orientation for the second driveline contact assembly and the retention orientation for the second driveline contact assembly.

In some embodiments, the blood circulation assist system includes separate, electrically isolated, conductive paths between the implanted blood pump and each of the first external controller and/or the second external controller so as to enable continued transmission of power and/or control signals to the implanted blood pump in the event of a discontinuity in one of the conductive paths. For example, in some embodiments of the blood circulation assist system, the distal driveline includes distal driveline redundant conductive leads. Each of the distal driveline redundant conductive leads provides a separate conductive path connecting one of the first side electrical contacts to the implantable blood pump and a corresponding one of the second side electrical contacts to the implantable blood pump. In some embodiments, at least two of the distal driveline redundant conductive leads are power leads and at least two of the distal driveline redundant conductive leads are ground leads so as to provide for redundant transmission of electrical power through the distal driveline to the implantable blood pump. In some embodiments, the first driveline includes first driveline redundant conductive leads. Each of the first driveline redundant conductive leads provides a separate conductive path connecting one of the first driveline electrical contacts to the first external controller. In some embodiments, at least two of the first driveline redundant conductive leads are power leads and at least two of the first driveline redundant conductive leads are ground leads so as to provide for redundant transmission of electrical power through the first driveline to the implantable blood pump. In some embodiments, the second driveline includes second driveline redundant conductive leads. Each of the second driveline redundant conductive leads provides a separate conductive path connecting one of the second driveline electrical contacts to the second external controller. In some embodiments, at least two of the second driveline redundant conductive leads are power leads and at least two of the second driveline redundant conductive leads are ground leads so as to provide for redundant transmission of electrical power through the second driveline to the implantable blood pump.

In another aspect, a connector assembly for connecting external power sources to an implantable medical device includes a distal driveline contact assembly, a first driveline contact assembly, and a second driveline contact assembly. The distal driveline contact assembly includes a first side coupling feature, first side electrical contacts, a second side coupling feature, a distal driveline first retention feature, and a distal driveline second retention feature. The first side electrical contacts are disposed on a first side of the distal driveline contact assembly and surround the first side coupling feature. The second side electrical contacts are disposed on a second side of the distal driveline contact assembly and surround the second side coupling feature. The first driveline contact assembly includes first driveline contact assembly electrical contacts and a first driveline contact assembly coupling feature. The first driveline contact assembly coupling feature is interfaced with the first side coupling feature to: (a) align the first driveline contact assembly electrical contacts with the first side electrical contacts, (b) accommodate engagement between the first driveline contact assembly electrical contacts and the first side electrical contacts, and (c) rotational couple the first driveline contact assembly with the distal driveline contact assembly and accommodate rotation of the first driveline contact assembly relative to the distal driveline contact assembly between a retention orientation for the first driveline contact assembly and a connection orientation for the first driveline contact assembly. In the retention orientation for the first driveline contact assembly, the distal driveline first retention feature blocks disconnection of the first driveline contact assembly from the distal driveline contact assembly. In the connection orientation for the first driveline contact assembly, the distal driveline contact assembly accommodates connection of the first driveline contact assembly to the distal driveline contact assembly and disconnection of the first driveline contact assembly from the distal driveline contact assembly. The second driveline contact assembly includes second driveline contact assembly electrical contacts and a second driveline contact assembly coupling feature. The second driveline contact assembly coupling feature is interfaced with the second side coupling feature to: (a) align the second driveline contact assembly electrical contacts with the second side electrical contacts, (b) accommodate engagement between the second driveline contact assembly electrical contacts and the second side electrical contacts, and (c) rotational couple the second driveline contact assembly with the distal driveline contact assembly and accommodate rotation of the second driveline contact assembly relative to the distal driveline contact assembly between a retention orientation for the second driveline contact assembly and a connection orientation for the second driveline contact assembly. In the retention orientation for the second driveline contact assembly, the distal driveline second retention feature blocks disconnection of the second driveline contact assembly from the distal driveline contact assembly. In the connection orientation for the second driveline contact assembly, the distal driveline contact assembly accommodates connection of the second driveline contact assembly to the distal driveline contact assembly and disconnection of the second driveline contact assembly from the distal driveline contact assembly.

In many embodiments, the connector assembly includes a shield assembly that is slidably mounted to the distal driveline contact assembly and reconfigurable between a retention configuration and a connection configuration. In many embodiments, while the shield assembly is in the retention configuration and the first driveline contact assembly is connected to the distal driveline contact assembly: (a) the shield assembly interfaces with each of the first driveline contact assembly and distal driveline contact assembly, and keeps the first driveline contact assembly in the retention orientation; and (b) the shield assembly blocks connection of the second driveline contact assembly to the distal driveline contact assembly. In many embodiments, while the shield assembly is in the connection configuration and the first driveline contact assembly is connected to the distal driveline contact assembly: (a) the shield assembly accommodates connection of the second driveline contact assembly to the distal driveline contact assembly; and (b) the shield assembly accommodates disconnection of the first driveline contact assembly from the distal driveline contact assembly. In many embodiments, while the shield assembly is in the retention configuration and the second driveline contact assembly is connected to the distal driveline contact assembly: (a) the shield assembly interfaces with each of the second driveline contact assembly and distal driveline contact assembly, and keeps the second driveline contact assembly in the retention orientation; and (b) the shield assembly blocks connection of the first driveline contact assembly to the distal driveline contact assembly.

The connector assembly can employ any suitable coupling features. For example, in some embodiments, the first side coupling feature includes a first pin that protrudes perpendicular to the first side, the second side coupling feature includes a second pin that protrudes perpendicular to the second side, the first driveline contact assembly coupling feature includes a first receptacle sized to receive and interface with the first pin; and the second driveline contact assembly coupling feature includes a second receptacle sized to receive and interface with the second pin.

In many embodiments of the connector assembly, electrical connection between the distal driveline and each of the first driveline and the second driveline is maintained during rotation of each of the first driveline connector assembly and the second driveline connector assembly relative to the distal driveline connector assembly. For example, in many embodiments of the connector assembly: (a) each of the first side electrical contacts extends along a respective circular arc so that contact is maintained between the first side electrical contact and a respective one of the first driveline electrical contacts while the first driveline contact assembly is rotated relative to the distal driveline contact assembly between the retention orientation for the first driveline contact assembly and the connection orientation for the first driveline contact assembly, and (b) each of the second side electrical contacts extends along a respective circular arc so that contact is maintained between the second side electrical contact and a respective one of the second driveline electrical contacts while the second driveline contact assembly is rotated relative to the distal driveline contact assembly between the connection orientation for the second driveline contact assembly and the retention orientation for the second driveline contact assembly.

In some embodiments, the connector assembly is configured to maintain connection between the distal driveline connector assembly and each of the first and second driveline connector assemblies while each of the first driveline connector assembly and the second driveline connector assembly is rotated relative to the distal driveline connector assembly. For example, in some embodiments of the connector assembly: (a) the first side electrical contacts comprise six first side electrical contacts, (b) the respective circular arc for each of the six first side electrical contacts extends through 90 degrees, (c) the second side electrical contacts comprise six second side electrical contacts, and (d) the respective circular arc for each of the six second side electrical contacts extends through 90 degrees. In some embodiments of the connector assembly, the first driveline contact assembly includes first driveline contact assembly compression springs. Each of the first driveline contact assembly compression springs biases a respective one of the first driveline contact assembly electrical contacts into contact with a respective one of the first side electrical contacts when the first driveline contact assembly is operatively coupled with the distal driveline contact assembly. In some embodiments of the connector assembly, the second driveline contact assembly includes second driveline contact assembly compression springs. Each of the second driveline contact assembly compression springs biases a respective one of the second driveline contact assembly electrical contacts into contact with a respective one of the second side electrical contacts when the second driveline contact assembly is operatively coupled with the percutaneous contact assembly.

For a fuller understanding of the nature and advantages of the present invention, reference should be made to the ensuing detailed description and accompanying drawings.

BRIEF DESCRIPTION OF THE DRAWINGS

FIG. 4 is a simplified schematic diagram illustrating the medical system of FIG. 1 in a fourth configuration in which, relative to the third configuration shown in FIG. 3, the first external controller assembly has been uncoupled from the implanted medical device via disconnection of the first driveline contact assembly from the distal driveline contact assembly.

FIG. 5 is a top view illustration of the first driveline contact assembly and the second driveline contact assembly connected to the distal driveline contact assembly in the configuration shown in FIG. 2.

FIG. 8 is a isometric view illustrating the first driveline contact assembly.

FIG. 9 is a cross-sectional view illustrating spring-loaded electrical contacts of the first driveline contact assembly.

FIG. 10 is a isometric view illustrating the distal driveline contact assembly connected to the first driveline contact assembly in a connection orientation for the first driveline contact assembly.

DETAILED DESCRIPTION

Figure 1:
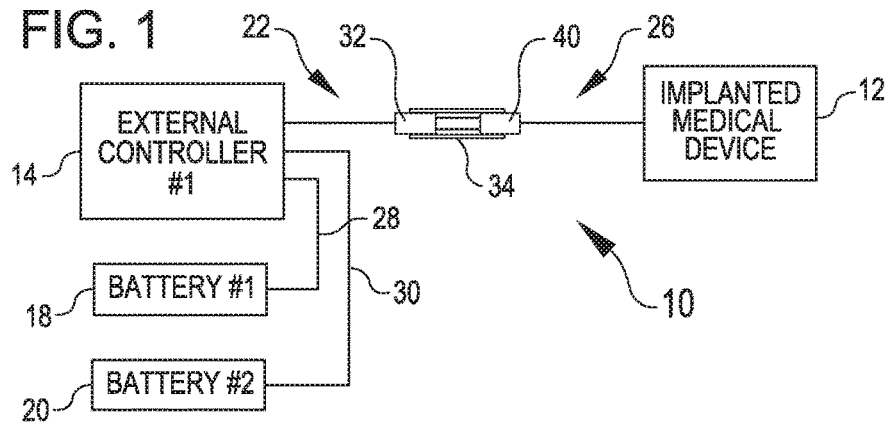
FIG. 1 is a simplified schematic diagram illustrating a medical system in a first configuration in which an implanted medical device is electrically coupled with a first external controller assembly via a first driveline contact assembly and a distal driveline contact assembly, in accordance with many embodiments.

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

The connector assembly described herein can be used in connection with any suitable implanted medical device. For example, in many embodiments, a ventricular assist device (e.g., a left ventricular assist device (LVAD)) can be electrically coupled with an external controller via a distal driveline (e.g., a percutaneous driveline). In many embodiments, the distal driveline transfers power to the LVAD. In some embodiments, the distal driveline provides a communication link between the external controller and the LVAD.

In the event of a fault in the external controller, it may be necessary to replace the faulted external controller to avoid potential detrimental disruption of operation of the LVAD. With some existing LVAD systems, replacement of a faulted controller involves disconnection of the faulted controller followed by connection a spare backup external controller. With such existing LVAD systems, when the faulted external controller is disconnected from the LVAD, the LVAD stops until the spare backup external controller is connected to the LVAD.

In many embodiments, the connector assembly described herein enables connection of the spare backup external controller to the LVAD prior to disconnection of the faulted external controller from the LVAD. As a result, stoppage of operation of the LVAD that may otherwise occur between disconnection of the faulted external controller from the LVAD and connection of the spare backup external controller to the LVAD can be avoided. Because the LVAD can be continuously operated during the replacement of the faulted external controller with the spare backup external controller, the replacement of the faulted external controller can be done in a manner that is healthier for the patient and reduces risk and anxiety.

Referring now to the drawings, in which like reference numerals represent like parts throughout the several views, FIGS. 1 through 4 show sequentially implementable configurations of a medical system 10. The medical system 10 includes an implanted medical device 12, a first external controller 14, a second external controller 16, a first battery 18, a second battery 20, a first driveline 22, a second driveline 24, a distal driveline 26, a first battery cable 28, and a second battery cable 30. The first driveline 22 is connected to the first external controller 14. In many embodiments, the first driveline 22 can be disconnected from the first external controller 14. The first driveline 22 includes a first driveline contact assembly 32, a first driveline shield assembly 34, and first driveline conductive leads over which electrical power is transmittable from the first external controller 14 to power operation of the implanted medical device 12. In many embodiments, the first driveline 22 includes one or more communication lines via which data and/or control signals are communicated between the first external controller 14 and the implanted medical device 12. The second driveline 24 is connected to the second external controller 16. In many embodiments, the second driveline 24 can be disconnected from the second external controller 16. The second driveline 24 includes a second driveline contact assembly 36, a second driveline shield assembly 38, and second driveline conductive leads over which electrical power is transmittable from the second external controller 16 to power operation of the implanted medical device 12. In many embodiments, the second driveline 24 includes one or more communication lines via which data and/or control signals are communicated between the second external controller 16 and the implanted medical device 12. The distal driveline 26 includes a distal driveline contact assembly 40 and distal driveline conductive leads over which electrical power is transmitted to power operation of the implanted medical device 12. In many embodiments, the distal driveline 26 includes one or more distal driveline communication leads via which data and/or control signals are communicated between the first external controller 14 and/or the second external controller 16 and the implanted medical device 12.

FIG. 1 shows a first configuration of the medical system 10 that corresponds to a normal operational configuration of the system 10. In the first configuration, the first driveline contact assembly 32 is connected to the distal driveline contact assembly 40, thereby operatively coupling the first driveline 22 with the distal driveline 26. In the first configuration, the first driveline contact assembly 32 is aligned with the distal driveline contact assembly 40 in a retention orientation for the first driveline contact assembly 32. In the retention of orientation for the first driveline contact assembly 32, as described in more detail herein, engagement between the first driveline contact assembly 32 and the distal driveline contact assembly 40 blocks disconnection of the first driveline contact assembly 32 from the distal driveline contact assembly 40. In the first configuration, the first driveline shield assembly 34 is in a retention configuration in which the first driveline shield assembly 34 is in contact with each of the first driveline contact assembly 32 and the distal driveline contact assembly 40 so as to prevent inadvertent disconnection of the first driveline contact assembly 32 from the distal driveline contact assembly 40 and/or to inhibit ingress of detrimental substances (e.g., moisture, dirt) into the interfacing first driveline electrical contacts and distal driveline electrical contacts. In the first configuration, the implanted medical device 12 is powered via electrical power transmitted from the first external controller 14 through the first driveline 22 and the distal driveline 26. In many embodiments, operation of the implanted medical device 12 is at least partially controlled via data and/or control signals communicated between the first external controller 14 and the implanted medical device 12. In many embodiments, power transmitted to the implanted medical device 12 from the first external controller 14 is supplied by the first battery 18 via the first battery cable 28 and/or the second battery 20 via the second battery cable 30. In many embodiments, the first configuration is employed in the absence of any fault in the first external controller 14 that would motivate replacement of the first external controller 14 with the second external controller 16.

Figure 2:
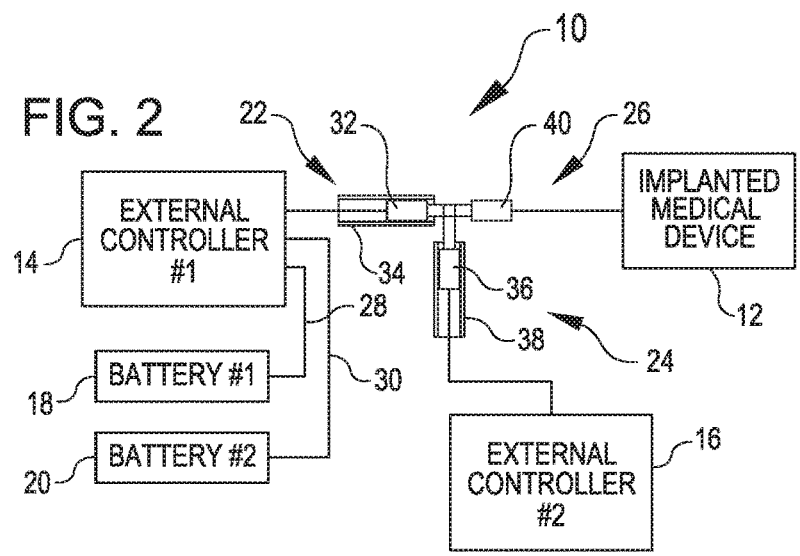
FIG. 2 is a simplified schematic diagram illustrating the medical system of FIG. 1 in a second configuration in which, relative to the first configuration shown in FIG. 1, the implanted medical device is further electrically coupled with a second external controller assembly via second driveline contact assembly connected to the distal driveline contact assembly.
Figure 3:
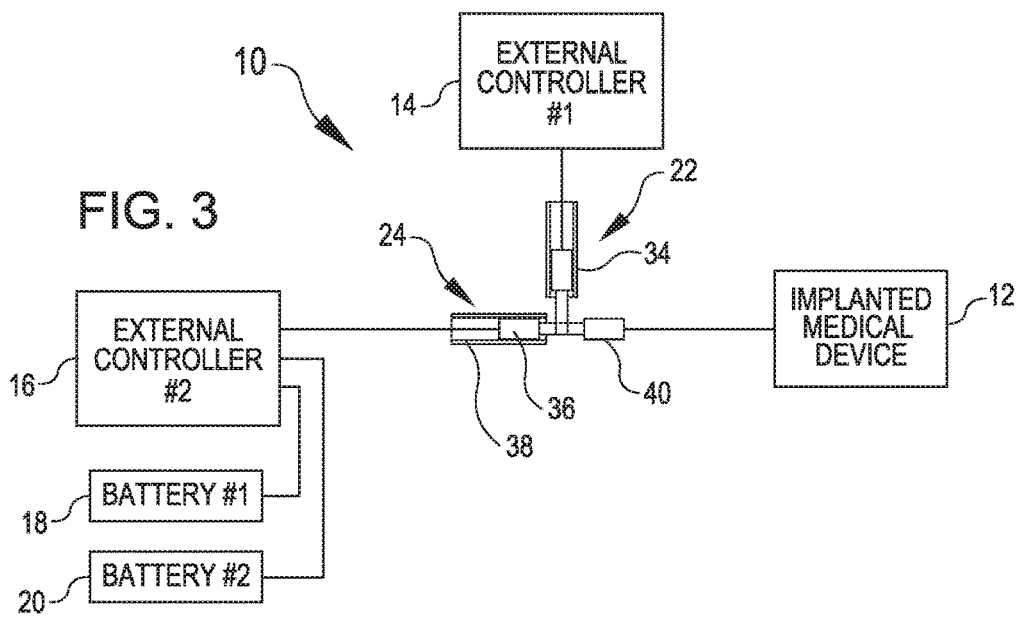
FIG. 3 is a simplified schematic diagram illustrating the medical system of FIG. 1 in a third configuration in which, relative to the second configuration shown in FIG. 2, the first driveline contact assembly has been rotated from a retention orientation to a connection orientation and the second driveline contact assembly has been rotated from a connection orientation to a retention orientation.

FIGS. 2 through 4 show a sequence of configurations of the medical system 10 by which the first external controller 14 can be replaced by the second external controller 16 without interrupting operation of the implanted medical device 12. FIG. 2 shows the medical system 10 in a second configuration in which, relative to the first configuration shown in FIG. 1, the implanted medical device 12 is further electrically coupled with the second external controller 16 via connection of the second driveline contact assembly 36 to the distal driveline contact assembly 40. To reconfigure the medical system 10 from the first configuration shown in FIG. 1 to the second configuration shown in FIG. 2, the first driveline shield assembly 34 is reconfigured from the retention configuration shown in FIG. 1 to a connection configuration shown in FIG. 2. In many embodiments, the first driveline shield assembly 34 is slidably coupled with the first driveline contact assembly 32 and is translated relative to the first driveline contact assembly 32 and the distal driveline contact assembly 40 from the retention configuration to the connection configuration. The distal driveline contact assembly 40 includes a first set of electrical contacts and a second set of electrical contacts. The first driveline contact assembly 32 can be selectively connected to the distal driveline contact assembly 40 via the first set of electrical contacts. Each of the distal driveline conductive leads is connected to a respective one of the first set of electrical contacts and to a respective one of the second set of electrical contacts. Each of the distal driveline communication leads is connected to a respective one of the first set of electrical contacts and to a respective one of the second set of electrical contacts. The second driveline contact assembly 36 can be selectively connected to the distal driveline contact assembly 40 via the second set of electrical contacts. With the first driveline shield assembly 34 in the connection configuration shown in FIG. 2, the second set of electrical contacts are exposed and the second driveline contact assembly 36 is connected with the distal driveline contact assembly 40 via the second set of electrical contacts. In the second configuration of the medical system 10 shown in FIG. 2, each of the distal driveline conductive leads is simultaneously electrically coupled with one of the first driveline conductive leads and a corresponding one of the second driveline conductive leads, thereby operatively connecting the first external controller 14 and the second external controller 16, in parallel, with the implanted medical device 12 so that electrical power can be supplied to the implanted medical device 12 by the first external controller 14 and/or by the second external controller 16. In the second configuration of the medical system 10 shown in FIG. 2, each of the distal driveline communication leads is simultaneously electrically coupled with one of the first driveline communication leads and a corresponding one of the second driveline communication leads, thereby operatively connecting the first external controller 14 and the second external controller 16, in parallel, with the implanted medical device 12 so that data and/or control signals can be exchanged between the implanted medical device 12 and the first external controller 14 and/or by the second external controller 16. A suitable communication protocol can be used to control communication between the first external controller 14, the second external controller 16, and the implanted medical device 12 in the second configuration of the medical system 10. In response to connection of the second driveline contact assembly 36 to the distal driveline contact assembly 40, any external control of the implanted medical device 12 by the first external controller 14 can be transferred to the second external controller 16 prior to disconnection of the first external controller 14.

FIG. 3 shows the medical system 10 in a third configuration in which, relative to the second configuration shown in FIG. 2, the first driveline contact assembly 32 has been rotated relative to the distal driveline contact assembly 40 from the retention orientation for the first driveline contact assembly 32 shown in FIG. 2 to a connection orientation for the first driveline contact assembly 32 shown in FIG. 3. In the illustrated embodiment, the connection orientation for the first driveline contact assembly 32 is 90 degrees from the retention orientation for the first driveline contact assembly 32. In the connection orientation for the first driveline contact assembly 32, as described in more detail herein, the first driveline contact assembly 32 can be disconnected from the distal driveline contact assembly 40. The second driveline contact assembly 36 has also been rotated relative to the distal driveline contact assembly 40 from the connection orientation for the second driveline contact assembly 36 to a retention orientation for the second driveline contact assembly 36. In the retention of orientation for the second driveline contact assembly 36, as described in more detail herein, engagement between the second driveline contact assembly 36 and the distal driveline contact assembly 40 blocks disconnection of the second driveline contact assembly 36 from the distal driveline contact assembly 40. Following connection of the second driveline contact assembly 36 to the distal driveline contact assembly 40, the first battery 18 and the second battery 20 can be transferred to the second external controller 16. For example, the first battery cable 28 can be disconnected from the first external controller 14 and then connected to the second external controller 16. Similarly, the second battery cable 30 can be disconnected from the first external controller 14 and then connected to the second external controller 16.

FIG. 4 shows the medical system 10 in a fourth configuration in which, relative to the third configuration shown in FIG. 3, the first driveline contact assembly 32 has been disconnected from the distal driveline contact assembly 40 and the second driveline shield assembly 38 has been reconfigured from the connection configuration for the second driveline shield assembly 38 and a retention configuration for the second driveline shield assembly 38. The fourth configuration shown in FIG. 4 is similar to the first configuration shown in FIG. 1 with the second external controller 16 being operatively coupled with the implanted medical device 12 in the fourth configuration shown in FIG. 4 instead of the first external controller 14 as in the first configuration shown in FIG. 1.

FIG. 5 is a top view illustration of the first driveline contact assembly 32 and the second driveline contact assembly 36 connected to the distal driveline contact assembly 40 in the second configuration shown in FIG. 2. In the retention orientation of the first driveline contact assembly 32 shown, a distal end 42 of the first driveline contact assembly 32 is retained within a complementarily-shaped slot 44 in the distal driveline contact assembly 40 and a proximal end 46 of the distal driveline contact assembly 40 is retained within a complementarily-shaped slot 48 in the first driveline contact assembly 32, thereby blocking disengagement of the first driveline electrical contacts from the first set of distal driveline electrical contacts. In the connection orientation of the second driveline contact assembly 36 shown, the second driveline contact assembly 36 is not retained via engagement with the distal driveline contact assembly 40, thereby accommodating connection of the second driveline contact assembly 36 to the distal driveline contact assembly 40 and disconnection of the second driveline contact assembly 36 from the distal driveline contact assembly 40. The first driveline shield assembly 34 and the second driveline shield assembly 38 are each in their respective connection configuration, thereby accommodating connection of the second driveline contact assembly 36 to the distal driveline contact assembly 40, disconnection of the second driveline contact assembly 36 from the distal driveline contact assembly 40, rotation of the first driveline contact assembly 32 relative to the distal driveline contact assembly 40 from the retention orientation for the first driveline contact assembly 32 shown in FIGS. 2 and 5 to the connection orientation for the first driveline contact assembly 32 shown in FIG. 3, and rotation of the second driveline contact assembly 36 relative to the distal driveline contact assembly 40 from the connection orientation for the second driveline assembly 36 shown in FIGS. 2 and 5 to the retention orientation for the second driveline assembly 36 shown in FIGS. 3 and 4. In the retention orientation of the second driveline contact assembly 36, similar to the retention orientation for the first driveline contact assembly 32, a distal end of the second driveline contact assembly 36 is retained within a complementarily-shaped slot in the distal driveline contact assembly 40 and the proximal end 46 of the distal driveline contact assembly 40 is retained within a complementarily-shaped slot in the second driveline contact assembly 36, thereby blocking disengagement of the second driveline electrical contacts from the second set of distal driveline electrical contacts.

Figure 6:
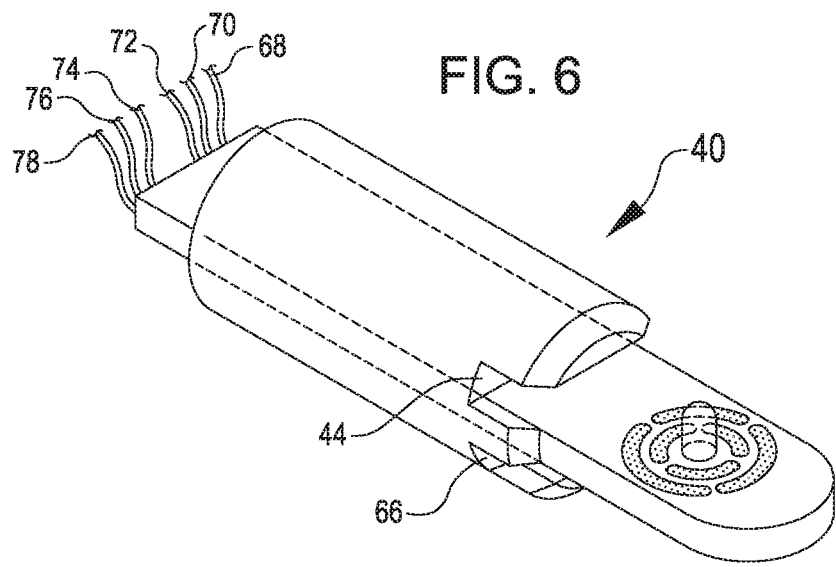
FIG. 6 is a isometric view illustration of the distal driveline contact assembly.
Figure 7:
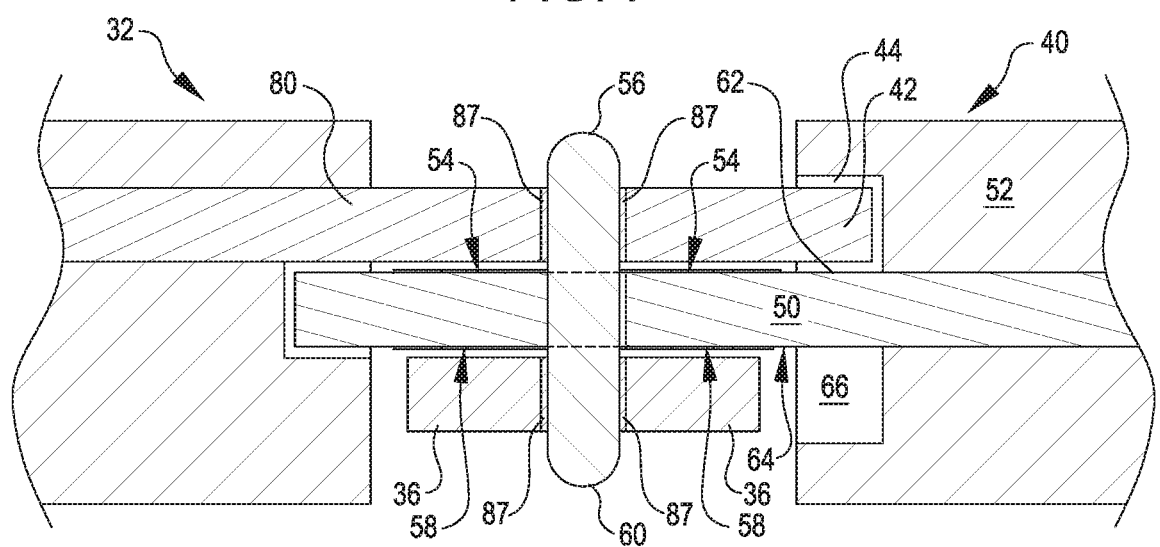
FIG. 7 is a cross-sectional view of the first driveline contact assembly and the second driveline contact assembly connected to the distal driveline contact assembly in the configuration shown in FIG. 2.

FIG. 6 is a isometric view illustration of the distal driveline contact assembly 40. FIG. 7 is a cross-sectional view of the first driveline contact assembly 32 connected to the distal driveline contact assembly 40 with the first driveline contact assembly 32 in the retention orientation for the first driveline contact assembly 32. The distal driveline contact assembly 40 includes a contact board assembly 50 and a base member 52. The contact board assembly 50 is fixedly mounted to the base member 52. The contact board assembly 50 includes the first set of distal driveline electrical contacts 54, a first protruding pin 56, the second set of distal driveline electrical contacts 58, and a second protruding pin 60. The first set of distal driveline electrical contacts 54 is disposed on a first planar surface 62 of the contact board assembly 50 and surround the first protruding pin 56. Each of the first set of distal driveline electrical contacts 54 has an arcuate shape and is sized and positioned to interface with a respective one of the first driveline electrical contacts in all orientations of the first driveline contact assembly 32 relative to the distal driveline contact assembly 40 from the retention orientation for the first driveline contact assembly 32 to the connection orientation for the first driveline contact assembly 32. The second set of distal driveline electrical contacts 58 is disposed on a second planar surface 64 of the contact board assembly 50 and surround the second protruding pin 60. In the illustrated embodiment, the second planar surface 64 is parallel to the first planar surface 62 and is disposed on an opposite side of the contact board assembly 50 relative to the first planar surface 62. Each of the second set of distal driveline electrical contacts 58 has an arcuate shape and is sized and positioned to interface with a respective one of the second driveline electrical contacts in all orientations of the second driveline contact assembly 36 relative to the distal driveline contact assembly 40 from the connection orientation for the second driveline contact assembly 36 to the retention orientation for the second driveline contact assembly 36. The base member 52 and the contact board assembly 50 form the slot 44 that retains the distal end 42 of the first driveline contact assembly 32 when the first driveline contact assembly 32 is connected to the distal driveline contact assembly 40 in the retention orientation for the first driveline contact assembly 32. The base member 52 and the contact board 50 also form a slot 66 that retains the distal end 68 of the second driveline contact assembly 36 when the second driveline contact assembly 36 is connected to the distal driveline contact assembly 40 in the retention orientation for the second driveline contact assembly 36. The contact board assembly 50 includes conductive paths by which the first set of distal driveline electrical connectors 54 and the second set of distal driveline electrical connectors 58 are electrically connected to the distal driveline conductive leads and the distal driveline communication leads. In the illustrated embodiment, the distal driveline conductive leads include a first positive lead 68, a first ground lead 70, a second positive lead 74, and a second ground lead 76, and the distal driveline communication leads include a first communication lead 72 and a second communication lead 78. The first positive lead 68 and the first ground lead 70 constitute a first set of power communication leads for transmission of electrical power over the distal driveline 26 to the implanted medical device 12. The second positive lead 74 and the second ground lead 76 constitute a second set of power communications leads for transmission of electrical power over the distal driveline 26 to the implanted medical device 12. The first and second positive leads 68, 74 and the first and second ground leads 70, 76 provide for redundant power transmission through the distal driveline 26 and enable continued power transmission through the distal driveline in the event of discontinuity of any one of the leads 68, 70, 74, 76. In a similar manner, the first and second communication leads 72, 78 provide for redundant communication over the distal driveline 26 to the implanted medical device 12 and enable continued communication over the distal driveline 26 to the implanted medical device 12 in the event of discontinuity of any one of the first and second communication leads 72, 78. Each of the distal driveline conductive leads 68, 70, 74, 74 is electrically connected with a respective one of the first set of distal driveline electrical contacts 54 and with a respective one of the second set of distal driveline electrical contacts 58. In a similar manner, each of the distal driveline communication leads 72, 78 is connected with a respective one of the first set of distal driveline electrical contacts 54 and with a respective one of the second set of distal driveline electrical contacts 58. The contact board assembly 50 can have any suitable configuration. For example, the contact board assembly 50 can have a multilayer configuration that includes embedded conductive traces that connect the first and second sets of the distal driveline electrical contacts 54, 58 with the distal driveline conductive leads 68, 70, 74, 76 and the distal driveline communication leads 72, 78.

In some embodiments, the first protruding pin 56 and the second protruding pin 60 are made from an electrically-conductive material and are electrically coupled to electrically connect respective communication contacts 87 of the first driveline contact assembly 32 and the second driveline contact assembly 36 to form a dedicated direct communication path between the first external controller 14 and the second external controller 16. In such embodiments, the dedicated direct communication path can be used for direct communication between the first external controller 14 and the second external controller 16 to transfer control of the implanted medical device 12 from the first external controller 14 to the second external controller 16 using any suitable approach, such as the approaches described herein. In some embodiments, each of the first set of distal driveline electrical contacts 54 and the second set of distal driveline electrical contacts 58 can have a dedicated direct communication contact that are electrically coupled with each other and adapted to interface with respective communication contacts of the first driveline contact assembly 32 and the second driveline contact assembly 36 to form a dedicated direct communication path between the first external controller 14 and the second external controller 16.

FIG. 8 is a isometric view illustration of the first driveline contact assembly 32 with the first driveline shield assembly 34 in the connection configuration. FIG. 9 is a cross-sectional view illustrating spring-loaded electrical contacts of the first driveline contact assembly 32. The configuration of the second driveline contact assembly 36 is the same as the first driveline contact assembly 32 so the following description of the first driveline contact assembly 32 applies to the second driveline contact assembly 36 and is therefore not repeated for the second driveline contact assembly 36. The first driveline contact assembly 32 includes a first driveline contact board assembly 80 and a first driveline base member 82. The first driveline contact board assembly 80 is fixedly mounted to the first driveline base member 82. The first driveline contact board assembly 80 includes first driveline spring-loaded electrical contacts 84 and a first driveline receptacle 86. In the illustrated embodiment, the first driveline electrical contacts 84 are spring-loaded assemblies that surround the first driveline receptacle 86 include spring-biased electrical contacts 88. Each of the electrical contacts 88 is positioned to interface with a respective one of the first set of driveline electrical contacts 56 throughout the range of range orientations of the first driveline contact assembly 32 from the retention orientation for the first driveline contact assembly 32 to the connection orientation for the first driveline contact assembly 32. The first driveline base member 82 and the first driveline contact board assembly 80 form the slot 48 that retains the proximal end 46 of the distal driveline contact assembly 40 when the first driveline contact assembly 32 is connected to the distal driveline contact assembly 40 in the retention orientation for the first driveline contact assembly 32. The first driveline contact board assembly 80 includes conductive paths by which the electrical contacts 88 are electrically connected to the first driveline conductive leads and the first driveline communication leads. In the illustrated embodiment, first driveline conductive leads include a first positive lead 88, a first ground lead 90, a second positive lead 94, and a second ground lead 96, and the first driveline communication leads include a first communication lead 92 and a second communication lead 98. The first positive lead 88 and the first ground lead 90 constitute a first set of power communication leads for transmission of electrical power over the first driveline 22 to the implanted medical device 12. The second positive lead 94 and the second ground lead 96 constitute a second set of power communications leads for transmission of electrical power over the first driveline 22 to the implanted medical device 12. The first and second positive leads 88, 94 and the first and second ground leads 90, 96 provide for redundant power transmission through the first driveline 22 and enable continued power transmission through the first driveline 22 in the event of discontinuity of any one of the leads 88, 90, 94, 96. In a similar manner, the first and second communication leads 92, 98 provide for redundant communication over the first driveline 22 to the implanted medical device 12 and enable continued communication over the first driveline 22 to the implanted medical device 12 in the event of discontinuity of any one of the first and second communication leads 92, 98. Each of the distal driveline conductive leads 88, 90, 94, 96 is electrically connected with a respective one of the spring-biased electrical contacts 88. In a similar manner, each of the distal driveline communication leads 92, 98 is connected with a respective one of the spring-biased electrical contacts 88. The first driveline contact board assembly 80 can have any suitable configuration. For example, the first driveline contact board assembly 80 can have a multilayer configuration that includes embedded conductive traces that connect the spring-biased electrical contacts 88 with the first driveline conductive leads 88, 90, 94, 96 and the first driveline communication leads 92, 98. In some embodiments, each of the first driveline contact assembly 32 and the second driveling contact assembly 36 connects a dedicated communication lead 93 with a respective dedicated communication contact (e.g., communication contact 87) and the distal driveline contact assembly 40 connects the respective dedicated communication contacts so that a dedicated communication path exists between the first external controller 14 and the second external controller 16 while both the first and second driveling contact assemblies 32, 36 are connected to the distal driveline contact assembly 40.

Figure 11:
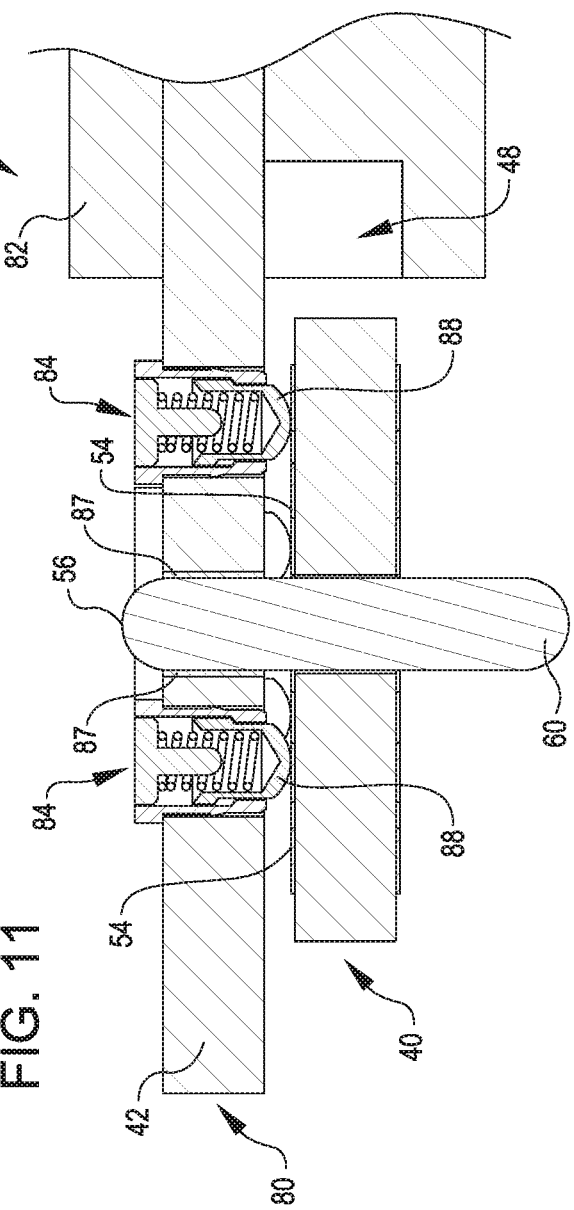
FIG. 11 shows a cross-sectional view through the distal driveline contact assembly and the first driveline contact assembly in the configuration shown in FIG. 10 showing engagement of the spring-loaded electrical contacts of the first driveline contact assembly and first side electrical contacts of the distal driveline contact assembly.

FIG. 10 is a isometric view illustrating the first driveline contact assembly 32 connected to the distal driveline contact assembly 40 in the connection orientation for the first driveline contact assembly 32. FIG. 11 shows a cross-sectional view through the first driveline contact assembly 32 and the distal driveline contact assembly 40 in the connection orientation for the first driveline contact assembly 32. FIG. 11 illustrates engagement of the spring-biased contacts 88 of the first driveline contact assembly 32 and the first set of electrical contacts of the distal driveline contact assembly 40. In the connection orientation for the first driveline contact assembly 32, the distal end 42 of the first driveline contact assembly 32 is disposed outside of the slot 44 in the distal driveline contact assembly 40 and the distal end 46 of the distal driveline contact assembly 40 is disposed outside the slot 48 in the first driveline contact assembly 32, thereby accommodating coupling of the first driveline contact assembly 32 to the distal driveline contact assembly 40 and decoupling of the first driveline contact assembly 33 from the distal driveline contact assembly 40.

Figure 12:
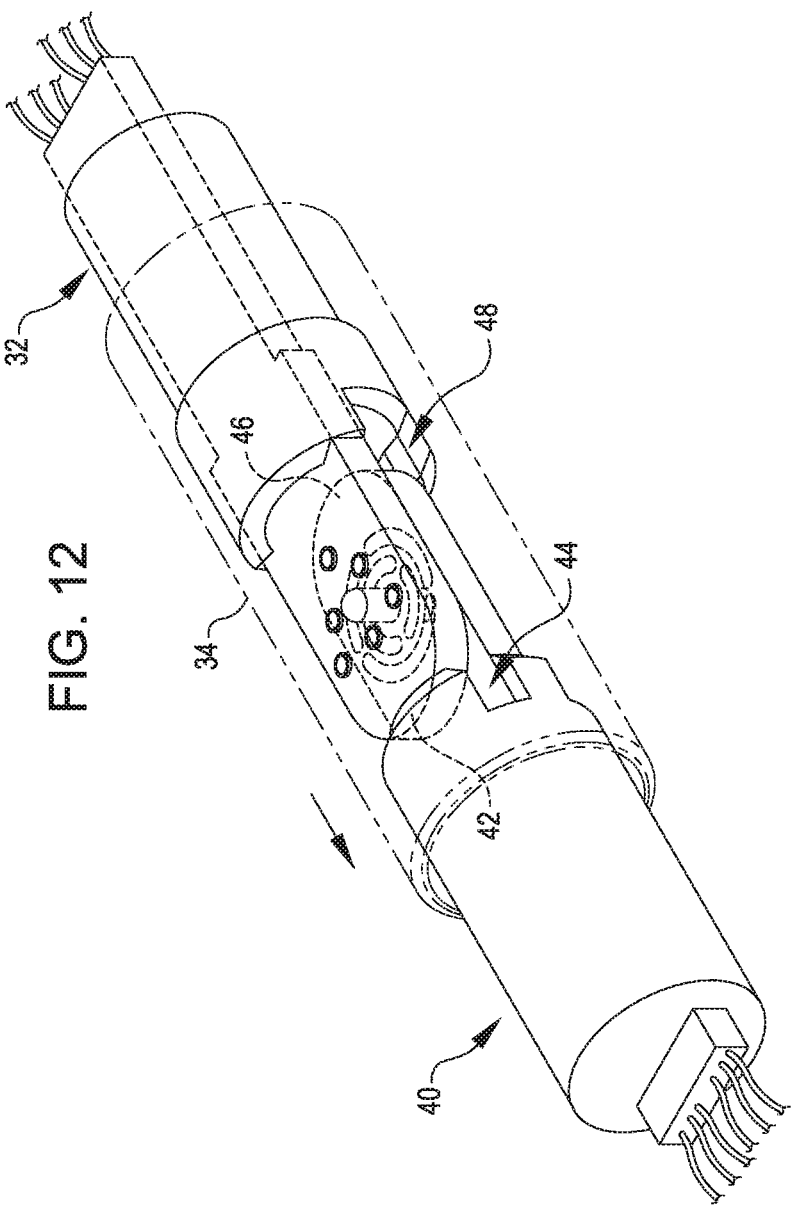
FIG. 12 is a isometric view illustrating the distal driveline contact assembly connected to the first driveline contact assembly in a retention orientation for the first driveline contact assembly.

FIG. 12 is a isometric view illustrating the first driveline contact assembly 32 connected to the distal driveline contact assembly 40 in the retention orientation for the first driveline contact assembly 32. In the retention orientation for the first driveline contact assembly 32, the distal end 42 of the first driveline contact assembly 32 is disposed in the slot 44 in the distal driveline contact assembly 40 and the distal end 46 of the distal driveline contact assembly 40 is disposed in the slot 48 in the first driveline contact assembly 32, thereby retaining the first driveline contact assembly 32 in engagement with the distal driveline contact assembly 40. In the configuration shown in FIG. 12, the first driveline shield assembly 34 is in the retention configuration, thereby shielding the connecting portions of the first driveline contact assembly 32 and the distal driveline contact assembly 40 from ingress of foreign substances (e.g., dirt, moisture), restraining the first driveline contact assembly 32 in the retention orientation for the first driveline contact assembly 32, and blocking coupling of the second driveline contact assembly 36 to the distal driveline contact assembly 40.

Figure 13:
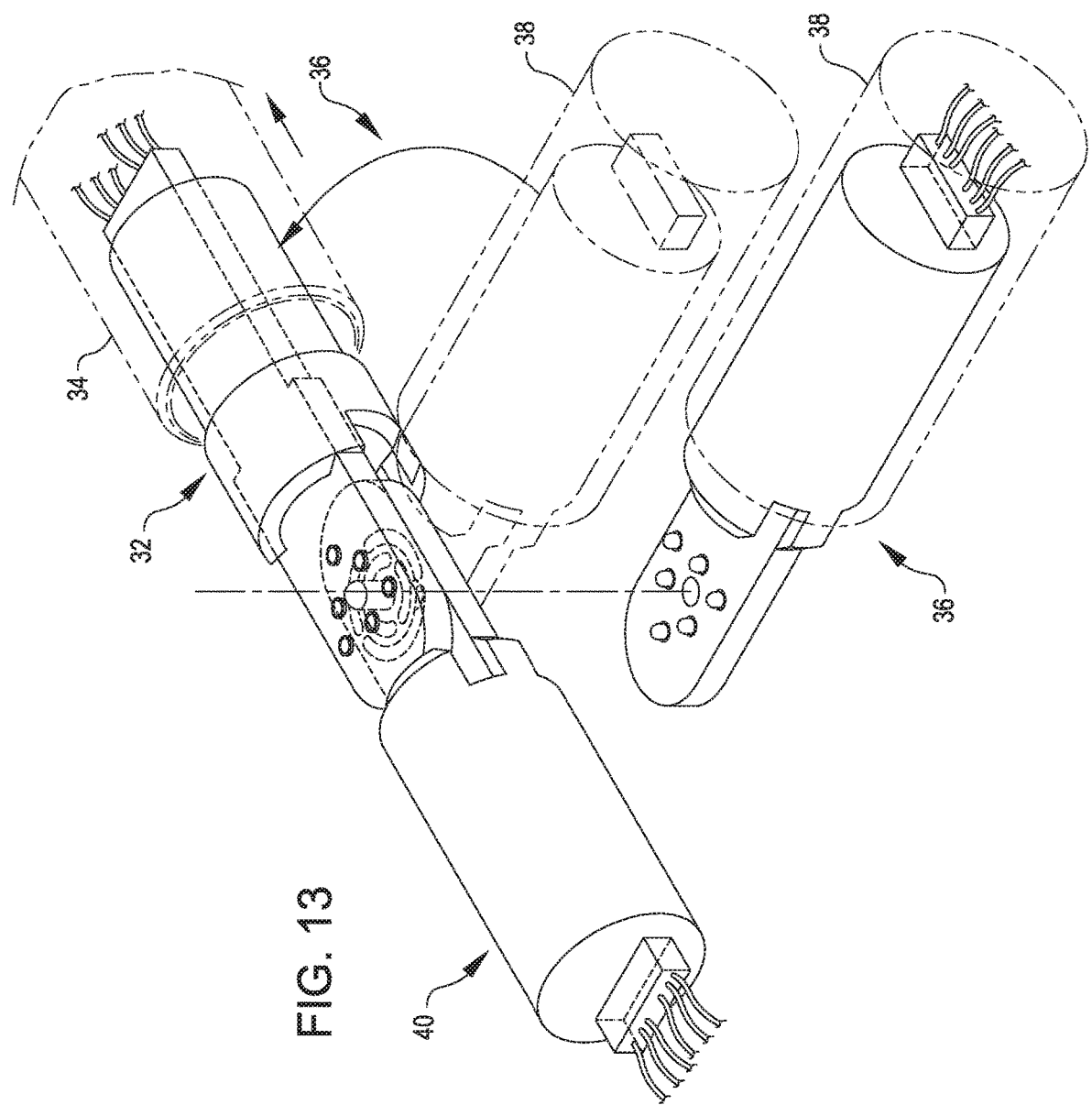
FIG. 13 is a isometric view illustrating connection of the second driveline contact assembly to the distal driveline contact assembly while the first driveline contact assembly remains connected to the distal driveline contact assembly.

FIG. 13 is a isometric view illustrating connection of the second driveline contact assembly 36 to the distal driveline contact assembly 40 while the first driveline contact assembly 32 remains connected to the distal driveline contact assembly 40. To accommodate connection of the second driveline contact assembly 36 to the distal driveline contact assembly 40, each of the first driveline shield assembly 34 and the second driveline shield assembly 38 is in their respective connection configuration.

Figure 14:
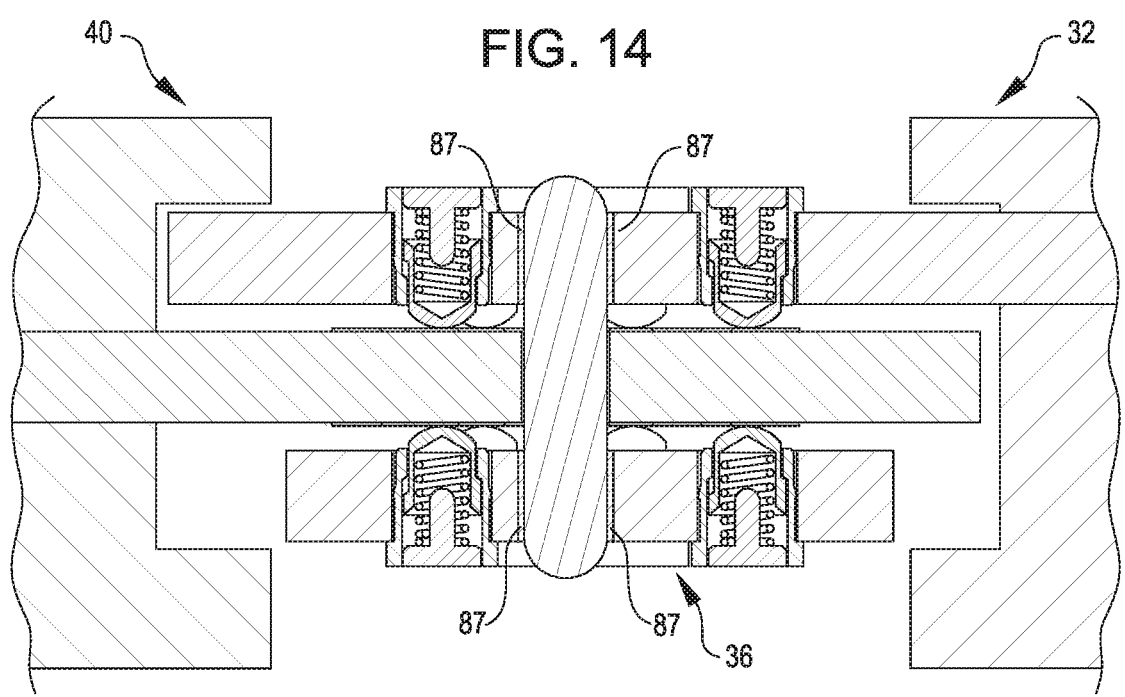
FIG. 14 shows a cross-sectional view through the distal driveline contact assembly, the first driveline contact assembly, and the second driveline contact assembly in the configuration shown in FIG. 5 showing engagement of the spring-loaded electrical contacts of the first and second driveline contact assemblies and electrical contacts of the distal driveline contact assembly.

FIG. 14 shows a cross-sectional view through the distal driveline contact assembly 40, the first driveline contact assembly 32, and the second driveline contact assembly 36 in the configuration shown in FIG. 5. In the illustrated configuration, spring-loaded electrical contacts of the first and second driveline contact assemblies 32, 36 engage respective and electrical contacts of the distal driveline contact assembly 40. In the illustrated embodiment, the first protruding pin 56 and the second protruding pin 60 are respective portions of a monolithic member made of a suitable conductive material (e.g., a suitable metal) and connect respective communication contacts 87 of the first and second driveling contact assemblies 32, 36 to provide a direct communication path between the first external controller 14 and the second external controller 16.

Figure 15:
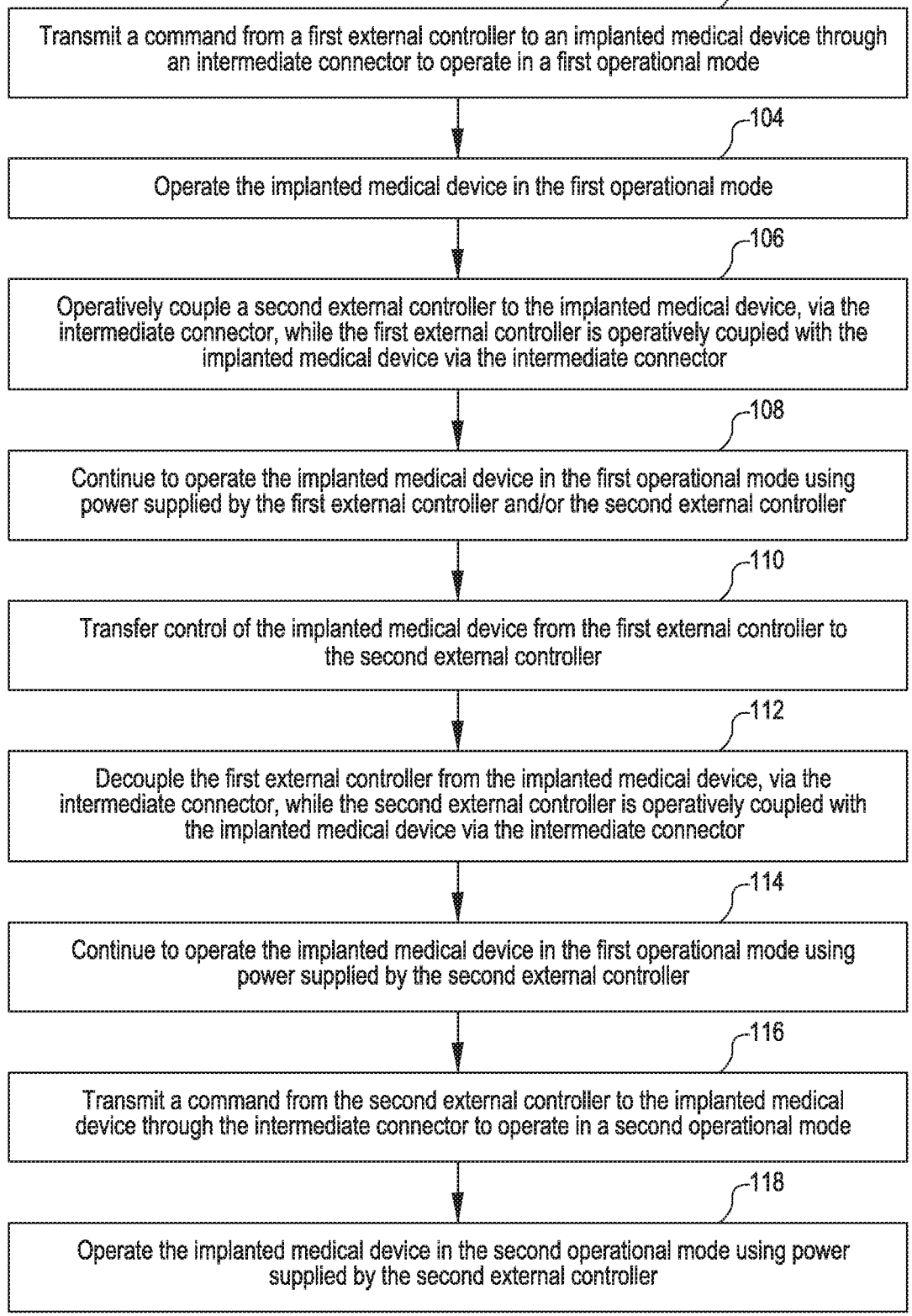
FIG. 15 is a simplified schematic diagram of a method of replacing an external controller of an implanted medical device with a replacement external controller while continuing to operate the implanted medical device, in accordance with many embodiments.

FIG. 15 is a simplified schematic diagram of a method 100 of replacing an external controller of an implanted medical device with a replacement external controller while continuing to operate the implanted medical device, in accordance with many embodiments. Any suitable medical system, such as the medical system 10 described herein, can be used to practice the method 100. Moreover, while the method 100 is described herein with reference to the medical system 10, any suitable medical system that includes an implanted medical device and a replaceable external controller for the implanted medical device can be used to practice the method 100.

In many embodiments, the implanted medical device 12 is configured to continue to operate in an operational mode specified by an external controller until commanded to switch to another operational mode specified by the same or different external controller. In such embodiments, as long as the implanted medical device 12 is provided with sufficient electrical power for operation (e.g., from the first external controller 14 and/or the second external controller 16), the implanted medical device 12 continues operation in the previously commanded operational mode during replacement of the first external controller 14 with the second external controller 16 and until commanded by the second external controller 16 to switch to another operational mode.

The method 100 includes transmitting a command from a first external controller (e.g., the first external controller 12) to an implanted medical device (e.g., the implanted medical device 12) through an intermediate connector (e.g., the distal driveline connector 40) to operate in a first operational mode (act 102). For example, when the implanted medical device includes a blood pump, the first operational mode can be any suitable operational mode of the blood pump (e.g., a continuous speed mode, a variable speed mode generating blood pulses in the user). The operational mode command can be transmitted from the first external controller to the implanted medical device using any suitable communication protocol (e.g., Local Interconnect Network (LIN)) over a suitable serial communication link (e.g., an RS-485 link, a Controller Area Network (CAN) bus). In response to receipt of the operational command by the implanted medical device, the implanted medical device operates in the first operational mode (act 104). The implanted medical device can be operated in the first operational mode using electrical power supplied via any one or more external controllers operatively coupled with the implanted medical device. In many embodiments, the implanted medical device continues to operate in the first operational mode until commanded to switch to another operational mode by either the first external controller or a second external controller that has assumed control of the implanted medical device from the first external controller.

In act 106 of the method 100, a second external controller is operatively coupled to the implanted medical device, via the intermediate connector, while the first external controller is operatively coupled with the implanted medical device via the intermediate connector. In many embodiments, upon connection of the second external controller to the implanted medical device via the intermediate connector, the implanted medical device continues to operate in the first operational mode using electrical power supplied via either the first external controller or the second external controller, or via both the first external controller and the second external controller (act 108).

Figure 16:
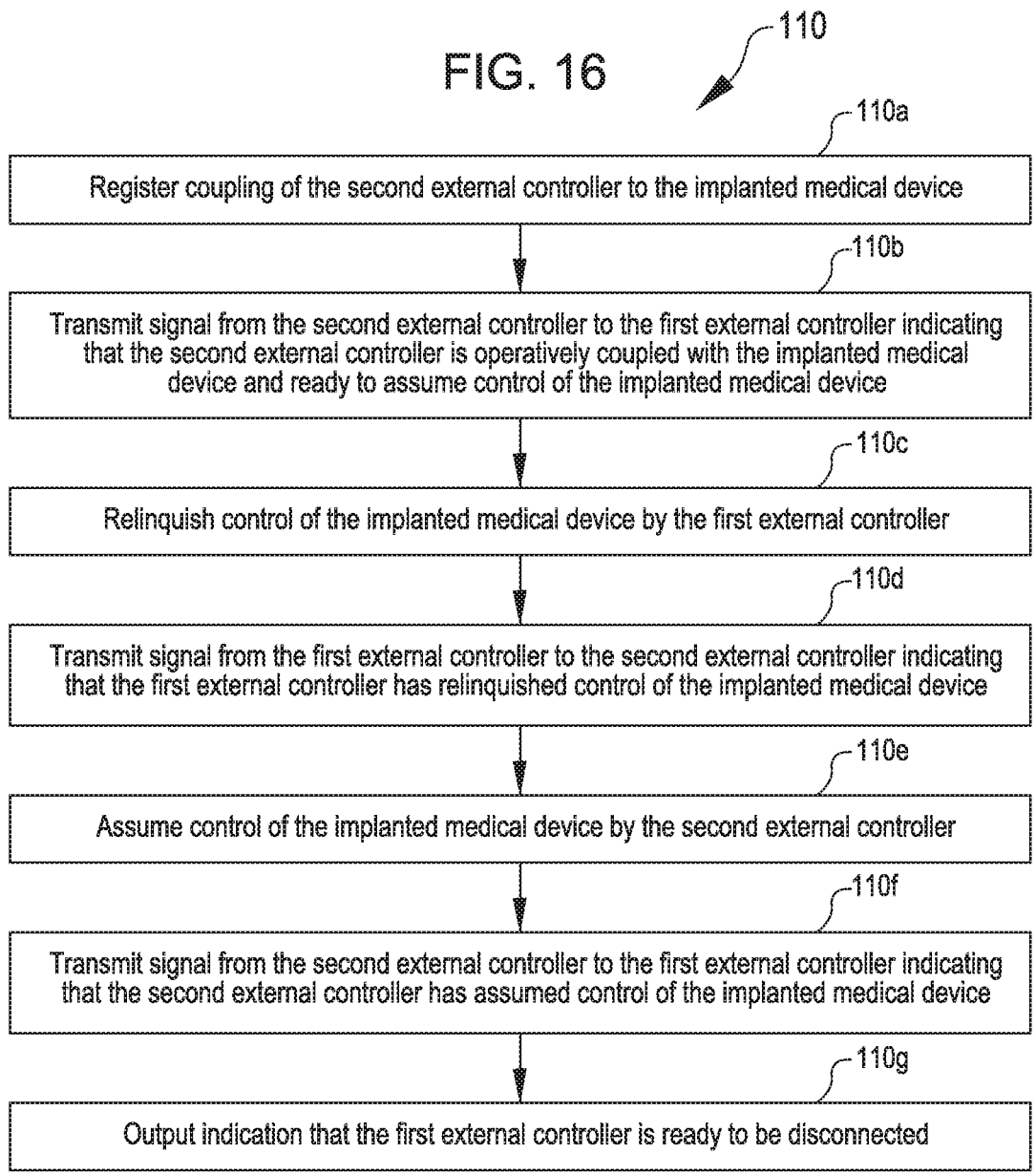
FIG. 16 is a simplified schematic diagram of acts for transferring control of the implanted medical device from the external controller to the replacement external controller in the method of FIG. 15.

In act 110 of the method 100, control of the implanted medical device is transferred from the first external controller to the second external controller. Any suitable approach can be used to transfer control of the implanted medical device from the first external controller to the second external controller. For example, FIG. 16 is a simplified schematic diagram of acts that can be accomplished to accomplish act 110 of the method 100. In act 110*a*, coupling of the second external controller to the implanted medical device is registered. In many embodiments, the registering of the coupling of the second external controller to the implanted medical device starts a process by which control of the implanted medical device is transferred from the first external controller to the second external controller. In some embodiments, the second external controller detects connection of the second external controller to the intermediate connector by sensing a voltage differential between the first positive lead 88 and the first ground lead 90 and/or between the second positive lead 94 and the second ground lead 96 associated with electrical power being supplied to the implanted medical device via the first external controller. In some embodiments, the second external controller detects connection of the second external controller to the intermediate connector by detecting communication between the first external controller and the implanted medical device via the first communication lead 92 and/or the second communication lead 98.

In response to the registration of the coupling of the second external controller to the implanted medical device, the second external controller transmits a signal to the first external controller that indicates that the second external controller is operatively coupled with the implanted medical device and is ready to assume control of the implanted medical device (act 110*b*). Any suitable approach can be used to transmit the signal from the second external controller to the first external controller including, but not limited to, via the first and second communication leads 92, 98 using a suitable communication protocol, via a dedicated direct communication path between the first and second external controllers as described herein, or via a suitable wireless transmission from the second external controller to the first external controller.

In response to receiving the signal from the second external controller that the second external controller is operatively coupled to the implanted medical device and ready to assume control of the implanted medical device, the first external controller relinquishes control of the implanted medical device (act 110*c*). After, or simultaneous with, relinquishing control of the implanted medical device by the first external controller, the first external controller transmits a signal to the second external controller that indicates that the first external controller has relinquished control of the implanted medical device (act 110*d*). Any suitable approach can be used to transmit the signal from the first external controller to the second external controller including, but not limited to, via the first and second communication leads 92, 98 using a suitable communication protocol, via a dedicated direct communication path between the first and second external controllers as described herein, or via a suitable wireless transmission from the first external controller to the second external controller.

In response to receiving the signal from the first external controller that the first external controller has relinquished control of the implanted medical device, the second external controller assumes control of the implanted medical device (act 110*e*). After, or simultaneous with, assuming control of the implanted medical device by the second external controller, the second external controller transmits a signal to the first external controller that indicates that the second external controller has assumed control of the implanted medical device (act 110*f*). Any suitable approach can be used to transmit the signal from the second external controller to the first external controller including, but not limited to, via the first and second communication leads 92, 98 using a suitable communication protocol, via a dedicated direct communication path between the first and second external controllers as described herein, or via a suitable wireless transmission from the second external controller to the first external controller.

In response to receiving the signal from the second external controller that the second external controller has assumed control of the implanted medical device, the first external controller outputs an indication that the first external controller is ready to be disconnected (act 110*g*). For example, in many embodiments the first external controller includes a display and a message is outputted on the display indicating that the first external controller is ready to be disconnected.

Referring back to FIG. 15, following the transfer of control of the implanted medical device from the first external controller to the second external controller in act 110, the first external controller is decoupled from the implanted medical device, via the intermediate connector, while the second external controller is operatively coupled with the implanted medical device via the intermediate connector (act 112). For example, in the medical system 10, the first external controller 14 is decoupled from the implanted medical device 12 by disconnecting the first driveline connector 32 from the distal driveline connector 40 while the second external controller 16 is operatively coupled with the implanted medical device 12 via connection between the second driveline connector 36 and the distal driveline connector 40. Subsequent to act 112, the method 100 further includes continuing to operate the implanted medical device in the first operational mode using power supplied by the second external controller (act 114). With the implanted medical device now under the control of the second external controller, the method can include transmitting a command from the second external controller to the implanted medical device through the intermediate connector to cause the implanted medical device to switch from operating in the first operational mode to operate in a second operational mode (act 116). The implanted medical device can then be operated in the second operational mode using power supplied by the second external controller (act 118).

Figure 17:
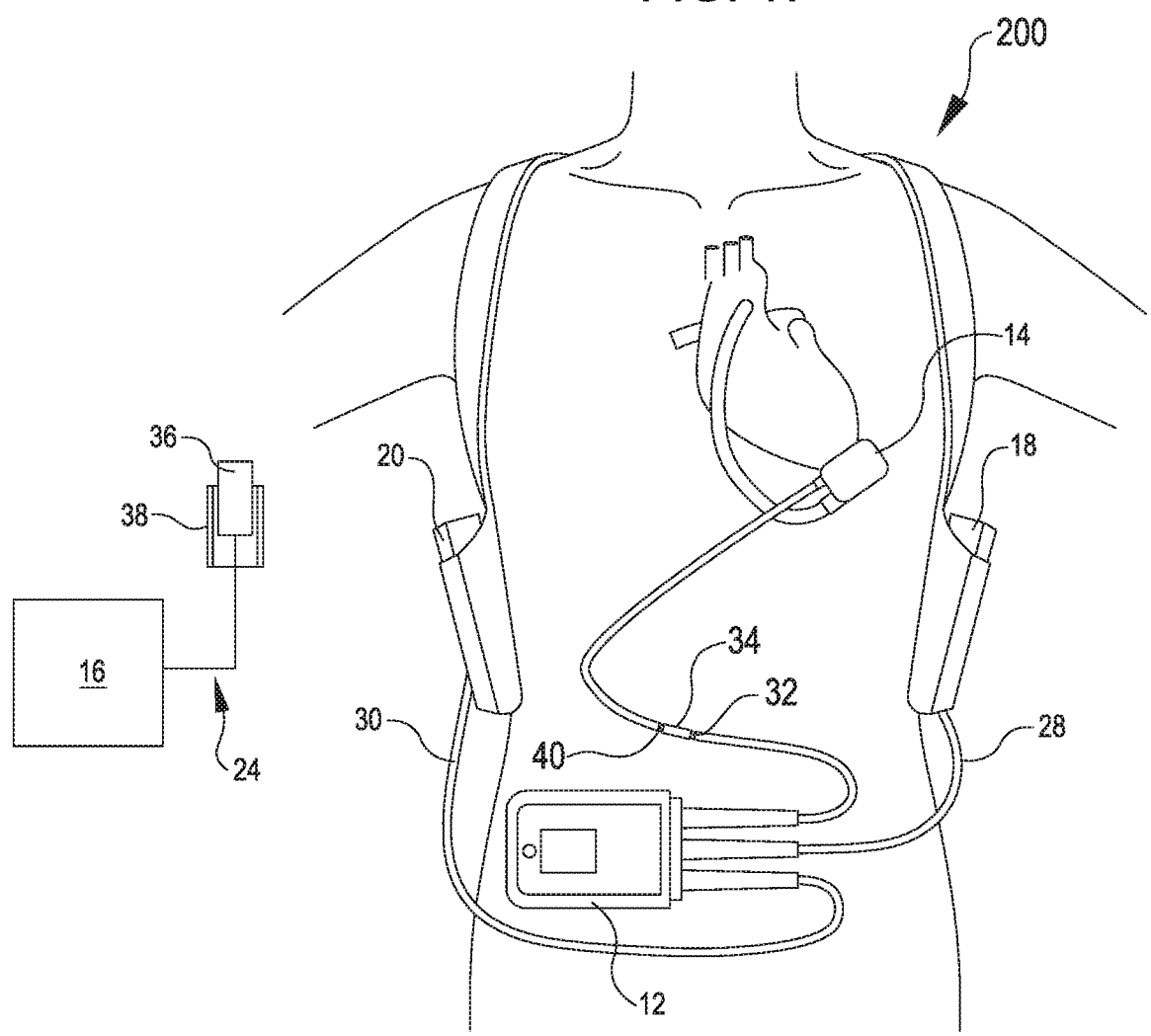
FIG. 17 is an illustration of a mechanical circulatory support system that includes the first driveline contact assembly, the second driveline contact assembly, and the distal driveline contact assembly.

FIG. 17 is an illustration of a mechanical circulatory support system 200 configured the same as the medical system 10 described herein, but with the implanted medical device 12 including an implanted ventricular assist device 12-VAD. Accordingly, the description of the medical system 10 herein is applicable to the mechanical circulatory support system 200 and is therefore not repeated here.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims. For example, the distal driveline contact assembly 40 can have a distal driveline shield assembly that is similar to each of the first and second driveline shield assemblies 34, 38 and the first and second driveline shield assemblies 34, 38 can be omitted.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A method of replacing a first external power supply that supplies electrical power to an implanted medical device with a second external power supply that supplies electrical power to the implanted medical device without interrupting supply of electrical power to the implanted medical device from at least one of the first external power supply and the second external power supply, the method comprising:

supplying electrical power to the implanted medical device from the first external power supply via a first driveline connected to the first external power supply and a distal driveline through which electrical power is transmitted to the implanted medical device, wherein the first driveline comprises a first driveline contact assembly, and wherein the distal driveline comprises a distal driveline contact assembly connected to the first driveline contact assembly and receiving electrical power from the first driveline contact assembly;

while the first external power supply is operatively connected to the implanted medical device via the first driveline contact assembly being connected to the distal driveline contact assembly, operatively connecting the second external power supply to the implanted medical device by connecting a second driveline contact assembly to the distal driveline contact assembly, wherein a second driveline connected to the second external power supply comprises the second driveline contact assembly;

rotating the first driveline contact assembly relative to the distal driveline contact assembly from a retention orientation to a connection orientation that accommodates disconnection of the first driveline contact assembly from the distal driveline contact assembly, wherein the first external power supply is operatively connected to the implanted medical device via the first driveline contact assembly being connected to the distal driveline contact assembly in the connection orientation; and while the second external power supply is operatively connected to the implanted medical device via the second driveline contact assembly being connected to the distal driveline contact assembly, disconnecting the first external power supply from the implanted medical device by disconnecting the first driveline contact assembly from the distal driveline contact assembly.

2. The method of claim 1, further comprising:
reconfiguring a shield assembly from a retention configuration to a connection configuration, wherein the shield assembly prevents disconnection of the first driveline contact assembly from the distal driveline contact assembly in the retention configuration, wherein the shield assembly accommodates the first driveline contact assembly and the second driveline contact assembly being concurrently connected to the distal driveline contact assembly in the connection configuration, and wherein the shield assembly accommodates disconnection of the first driveline contact assembly from the distal driveline contact assembly in the connection configuration; and subsequent to the disconnection of the first driveline contact assembly from the distal driveline contact assembly, reconfiguring the shield assembly from the connection configuration to the retention configuration, wherein the shield assembly, in the retention configuration, prevents disconnection of the second driveline contact assembly from the distal driveline contact assembly.

3. The method of claim 2, further comprising:
prior to the reconfiguring of the shield assembly from the connection configuration to the retention configuration, rotating the second driveline contact assembly relative to the distal driveline contact assembly from a connection orientation for the second driveline contact assembly in which the distal driveline contact assembly accommodates connection of the second driveline contact assembly with the distal driveline contact assembly to a retention orientation for the second driveline contact assembly.

4. The method of claim 3, wherein:
the reconfiguring of the shield assembly from the retention configuration to the connection configuration comprises translating the shield assembly relative to the first driveline contact assembly and the distal driveline contact assembly to disengage the shield assembly from at least one of the first driveline contact assembly and the distal driveline contact assembly; and the reconfiguring of the shield assembly from the connection configuration to the retention configuration comprises translating the shield assembly relative to the second driveline contact assembly and the distal driveline contact assembly to engage the shield assembly with at least one of the second driveline contact assembly and the distal driveline contact assembly.

5. The method of claim 3, wherein:
the distal driveline contact assembly blocks disconnection of the first driveline contact assembly from the distal driveline contact assembly while the first driveline contact assembly is in the retention orientation relative to the distal driveline contact assembly; and the distal driveline contact assembly blocks disconnection of the second driveline contact assembly from the distal driveline contact assembly while the second driveline contact assembly is in the retention orientation relative to the distal driveline contact assembly.

6. The method of claim 3, wherein:
the disconnection of the first driveline contact assembly from the distal driveline contact assembly comprises removing a first protruding pin of the distal driveline contact assembly from a recess of the first driveline contact assembly, electrical contacts of the first driveline contact assembly being aligned with first electrical contacts of the distal driveline contact assembly when the first protruding pin is disposed in the recess of the first driveline contact assembly; and the connection of the second driveline contact assembly to the distal driveline contact assembly comprises inserting a second protruding pin of the distal driveline contact assembly into a recess of the second driveline contact assembly to align electrical contacts of the second driveline contact assembly with second electrical contacts of the distal driveline contact assembly.

7. The method of claim 6, comprising maintaining contact between the electrical contacts of the second driveline contact assembly and the second electrical contacts of the distal driveline contact assembly during the rotating of the second driveline contact assembly relative to the distal driveline contact assembly.

8. The method of claim 1, wherein the implanted medical device comprises a blood pump.

9. A blood circulation assist system, comprising:
an implantable blood pump;
a first external controller;
a first driveline connected to the first external controller and through which electrical power is transmittable via the first external controller to the implantable blood pump;
a first driveline contact assembly electrically connected to the first driveline;
a second external controller;

a second driveline connected to the second external controller and through which electrical power is transmittable via the second external controller to the implantable blood pump;
a second driveline contact assembly electrically connected to the second driveline;
a distal driveline through which electrical power is transmitted to the implantable blood pump; and
a distal driveline contact assembly electrically connected to the distal driveline, the distal driveline contact assembly being electrically connectable to:
either of the first driveline contact assembly and the second driveline contact assembly; and
either of the first driveline contact assembly and the second driveline contact assembly while being connected to the other of the first driveline contact assembly and the second driveline contact assembly.

10. The blood circulation assist system of claim 9, wherein:
while the first driveline contact assembly is connected to the distal driveline contact assembly, the first driveline contact assembly is rotatable relative to the distal driveline contact assembly between a retention orientation for the first driveline contact assembly and a connection orientation for the first driveline contact assembly;
while the first driveline contact assembly is connected to the distal driveline contact assembly and in the retention orientation for the first driveline contact assembly, the first driveline contact assembly is engaged with the distal driveline contact assembly to maintain connection of the first driveline contact assembly with the distal driveline contact assembly; and
while the first driveline contact assembly is in the connection orientation for the first driveline contact assembly, the first driveline contact assembly can be connected to the distal driveline contact assembly and disconnected from the distal driveline contact assembly.

11. The blood circulation assist system of claim 9, wherein:
while the second driveline contact assembly is connected to the distal driveline contact assembly, the second driveline contact assembly is rotatable relative to the distal driveline contact assembly between a connection orientation for the second driveline contact assembly and a retention orientation for the second driveline contact assembly;
while the second driveline contact assembly is connected to the distal driveline contact assembly and in the retention orientation for the second driveline contact assembly, the second driveline contact assembly is engaged with the distal driveline contact assembly to maintain connection of the second driveline contact assembly with the distal driveline contact assembly; and
while the second driveline contact assembly is in the connection orientation for the second driveline contact assembly, the second driveline contact assembly can be connected to the distal driveline contact assembly and disconnected from the distal driveline contact assembly.

12. The blood circulation assist system of claim 11, further comprising one or more shield assemblies, each of the one or more shield assemblies being reconfigurable between a retention configuration and a connection configuration, wherein:

while one of the one or more shield assemblies is in the retention configuration and the first driveline contact assembly is connected to the distal driveline contact assembly:
the shield assembly interfaces with each of the first driveline contact assembly and distal driveline contact assembly, and keeps the first driveline contact assembly in the retention orientation for the first driveline contact assembly; and
the shield assembly blocks connection of the second driveline contact assembly to the distal driveline contact assembly;
while one of the one or more shield assemblies is in the connection configuration and the first driveline contact assembly is connected to the distal driveline contact assembly:
the shield assembly accommodates connection of the second driveline contact assembly to the distal driveline contact assembly; and
the shield assembly accommodates disconnection of the first driveline contact assembly from the distal driveline contact assembly; and
while one of the one or more shield assemblies is in the retention configuration and the second driveline contact assembly is connected to the distal driveline contact assembly:
the shield assembly interfaces with each of the second driveline contact assembly and distal driveline contact assembly, and keeps the second driveline contact assembly in the retention orientation for the second driveline contact assembly; and
the shield assembly blocks connection of the first driveline contact assembly to the distal driveline contact assembly.

13. The blood circulation assist system of claim 11, wherein:
the distal driveline contact assembly comprises
a first pin that protrudes perpendicular to a first side of the distal driveline contact assembly;
first side electrical contacts disposed on the first side;
a second pin that protrudes perpendicular to a second side of the distal driveline contact assembly; and
second side electrical contacts disposed on the second side;
the first driveline contact assembly comprises
first driveline electrical contacts; and
a first receptacle sized to receive and interface with the first pin and positioned to align the first driveline electrical contacts with the first side electrical contacts,
wherein engagement between the first driveline contact assembly and the distal driveline contact assembly while the first driveline contact assembly is connected to the distal driveline contact assembly and in the retention orientation for the first driveline contact assembly blocks disengagement of the first driveline electrical contacts from the first side electrical contacts; and
the second driveline contact assembly comprises
second driveline electrical contacts; and
a second receptacle sized to receive and interface with the second pin and positioned to align the second driveline electrical contacts with the second side electrical contacts,
wherein engagement between the second driveline contact assembly and the distal driveline contact assembly while the second driveline contact assembly is connected to the distal driveline contact assembly and in the retention orientation for the second driveline contact assembly blocks disengagement of the second driveline electrical contacts from the second side electrical contacts.

14. The blood circulation assist system of claim 13, wherein:
each of the first side electrical contacts extends along a respective circular arc so that contact can be maintained between the first side electrical contact and a respective one of the first driveline electrical contacts while the first driveline contact assembly is rotated relative to the distal driveline contact assembly between the retention orientation for the first driveline contact assembly and the connection orientation for the first driveline contact assembly; and
each of the second side electrical contacts extends along a respective circular arc so that contact can be maintained between the second side electrical contact and a respective one of the second driveline electrical contacts while the second driveline contact assembly is rotated relative to the distal driveline contact assembly between the connection orientation for the second driveline contact assembly and the retention orientation for the second driveline contact assembly.

15. The blood circulation assist system of claim 13, wherein:
the distal driveline comprises distal driveline redundant conductive leads;
each of the distal driveline redundant conductive leads provides a separate, electrically isolated, conductive path electrically coupling one of the first side electrical contacts to the implantable blood pump and a corresponding one of the second side electrical contacts to the implantable blood pump;
at least two of the distal driveline redundant conductive leads are power leads and at least two of the distal driveline redundant conductive leads are ground leads so as to provide for redundant transmission of electrical power through the distal driveline to the implantable blood pump;
the first driveline comprises first driveline redundant conductive leads;
each of the first driveline redundant conductive leads provides a separate, electrically isolated, conductive path connecting one of the first driveline electrical contacts to the first external controller;
at least two of the first driveline redundant conductive leads are power leads and at least two of the first driveline redundant conductive leads are ground leads so as to provide for redundant transmission of electrical power through the first driveline;
the second driveline comprises second driveline redundant conductive leads;
each of the second driveline redundant conductive leads provides a separate, electrically isolated, conductive path connecting one of the second driveline electrical contacts to the second external controller; and
at least two of the second driveline redundant conductive leads are power leads and at least two of the second driveline redundant conductive leads are ground leads so as to provide for redundant transmission of electrical power through the second driveline.

16. A connector assembly for connecting external power sources to an implanted medical device, the connector assembly comprising:
a distal driveline contact assembly comprising:
a first side coupling feature;
two or more first side electrical contacts disposed on a first side of the distal driveline contact assembly and surrounding the first side coupling feature;
a second side coupling feature; and
two or more second side electrical contacts disposed on a second side of the distal driveline contact assembly and surrounding the second side coupling feature;
a first driveline contact assembly comprising:
two or more first driveline contact assembly electrical contacts; and
a first driveline contact assembly coupling feature that can be interfaced with the first side coupling feature to:
align the first driveline contact assembly electrical contacts with the first side electrical contacts,
accommodate engagement between the first driveline contact assembly electrical contacts and the first side electrical contacts, and
rotationally couple the first driveline contact assembly with the distal driveline contact assembly and accommodate rotation of the first driveline contact assembly relative to the distal driveline contact assembly between a retention orientation for the first driveline contact assembly in which engagement of the first driveline contact assembly with the distal driveline contact assembly blocks disconnection of the first driveline contact assembly from the distal driveline contact assembly to a connection orientation for the first driveline contact assembly in which the distal driveline contact assembly accommodates disconnection of the first driveline contact assembly from the distal driveline contact assembly, wherein the first driveline contact assembly electrical contacts and the first side electrical contacts are configured for continuous electrical engagement from the retention orientation for the first driveline contact assembly to the connection orientation for the first driveline contact assembly; and
a second driveline contact assembly comprising:
two or more second driveline contact assembly electrical contacts; and
a second driveline contact assembly coupling feature that can be interfaced with the second side coupling feature to:
align the second driveline contact assembly electrical contacts with the second side electrical contacts,
accommodate engagement between the second driveline contact assembly electrical contacts and the second side electrical contacts, and
rotationally couple the second driveline contact assembly with the distal driveline contact assembly and accommodate rotation of the second driveline contact assembly relative to the distal driveline contact assembly between a connection orientation for the second driveline contact assembly in which the distal driveline contact assembly accommodates connection of the second driveline contact assembly to the distal driveline contact assembly and a retention orientation for the second driveline contact assembly in which engagement of the distal driveline contact assembly with the distal driveline contact assembly blocks disconnection of the second driveline contact assembly from the distal driveline contact assembly, wherein the second driveline contact assembly electrical contacts and the second side electrical contacts are configured for continuous electrical engagement from the connection orientation for the second driveline contact assembly to the retention orientation for the second driveline contact assembly.

17. The connector assembly of claim 16, further comprising one or more shield assemblies that are reconfigurable between a retention configuration and a connection configuration, wherein:
while one of the one or more shield assemblies is in the retention configuration and the first driveline contact assembly is connected to the distal driveline contact assembly
the shield assembly interfaces with each of the first driveline contact assembly and distal driveline contact assembly, and keeps the first driveline contact assembly in the retention orientation for the first driveline contact assembly; and
the shield assembly blocks connection of the second driveline contact assembly to the distal driveline contact assembly;
while one of the one or more shield assemblies is in the connection configuration and the first driveline contact assembly is connected to the distal driveline contact assembly
the shield assembly accommodates connection of the second driveline contact assembly to the distal driveline contact assembly; and
the shield assembly accommodates disconnection of the first driveline contact assembly from the distal driveline contact assembly; and
while one of the one or more shield assemblies is in the retention configuration and the second driveline contact assembly is connected to the distal driveline contact assembly
the shield assembly interfaces with each of the second driveline contact assembly and distal driveline contact assembly, and keeps the second driveline contact assembly in the retention orientation for the second driveline contact assembly; and
the shield assembly blocks connection of the first driveline contact assembly to the distal driveline contact assembly.

18. The connector assembly of claim 16, wherein:
the first side coupling feature comprises a first pin that protrudes perpendicular to the first side of the distal driveline contact assembly;
the second side coupling feature comprises a second pin that protrudes perpendicular to the second side of the distal driveline contact assembly;
the first driveline contact assembly coupling feature comprises a first receptacle sized to receive and interface with the first pin; and
the second driveline contact assembly coupling feature comprises a second receptacle sized to receive and interface with the second pin.

19. The connector assembly of claim 16, wherein:
each of the first side electrical contacts extends along a respective circular arc so that contact can be maintained between the first side electrical contact and a respective one of the first driveline contact assembly electrical contacts while the first driveline contact assembly is rotated relative to the distal driveline contact assembly between the retention orientation for the first driveline contact assembly and the connection orientation for the first driveline contact assembly; and
each of the second side electrical contacts extends along a respective circular arc so that contact can be maintained between the second side electrical contact and a respective one of the second driveline contact assembly electrical contacts while the second driveline contact assembly is rotated relative to the distal driveline contact assembly between the connection orientation for the second driveline contact assembly and the retention orientation for the second driveline contact assembly.

20. The connector assembly of claim 19, wherein:
the first side electrical contacts comprise six first side electrical contacts;
the respective circular arc for each of the six first side electrical contacts extends through 90 degrees;
the second side electrical contacts comprise six second side electrical contacts; and
the respective circular arc for each of the six second side electrical contacts extends through 90 degrees.

21. The connector assembly of claim 19, wherein:
the first driveline contact assembly comprises first driveline contact assembly compression springs, each of the first driveline contact assembly compression springs biasing a respective one of the first driveline contact assembly electrical contacts into contact with a respective one of the first side electrical contacts when the first driveline contact assembly is operatively coupled with the distal driveline contact assembly; and
the second driveline contact assembly comprises second driveline contact assembly compression springs, each of the second driveline contact assembly compression springs biasing a respective one of the second driveline contact assembly electrical contacts into contact with a respective one of the second side electrical contacts when the second driveline contact assembly is operatively coupled with the distal driveline contact assembly.

* * * * *